(12) United States Patent
Santini, Jr. et al.

(10) Patent No.: US 8,403,915 B2
(45) Date of Patent: Mar. 26, 2013

(54) MULTI-OPENING RESERVOIR DEVICES FOR CONTROLLED RELEASE OR EXPOSURE OF RESERVOIR CONTENTS

(75) Inventors: John T. Santini, Jr., North Chelmsford, MA (US); Zouhair Sbiaa, Everett, MA (US); Jonathan R. Coppeta, Windham, MA (US); Scott A. Uhland, San Jose, CA (US); Norman F. Sheppard, Jr., New Ipswich, NH (US)

(73) Assignee: MicroCHIPS, Inc., Waltham, MA (US)

( * ) Notice: Subject to any disclaimer, the term of this patent is extended or adjusted under 35 U.S.C. 154(b) by 49 days.

(21) Appl. No.: 12/581,558

(22) Filed: Oct. 19, 2009

(65) Prior Publication Data

US 2010/0042075 A1 Feb. 18, 2010

Related U.S. Application Data

(63) Continuation of application No. 11/217,799, filed on Sep. 1, 2005, now Pat. No. 7,604,628.

(60) Provisional application No. 60/606,387, filed on Sep. 1, 2004.

(51) Int. Cl.
*A61K 9/22* (2006.01)
*A61M 5/14* (2006.01)

(52) U.S. Cl. ............ 604/891.1; 604/890.1; 604/256

(58) Field of Classification Search .......... 604/244, 604/246, 256, 890.1
See application file for complete search history.

(56) References Cited

U.S. PATENT DOCUMENTS

| | | |
|---|---|---|
| 3,692,027 A | 9/1972 | Ellinwood, Jr. |
| 3,952,741 A | 4/1976 | Baker |
| 4,003,379 A | 1/1977 | Ellinwood, Jr. |
| 4,146,029 A | 3/1979 | Ellinwood, Jr. |
| 4,360,019 A | 11/1982 | Portner et al. |
| 4,507,115 A | 3/1985 | Kambara et al. |
| 4,585,652 A | 4/1986 | Miller et al. |
| 4,731,049 A | 3/1988 | Parsi |
| 4,731,051 A | 3/1988 | Fischell |
| 4,793,825 A | 12/1988 | Benjamin et al. |
| 4,994,023 A | 2/1991 | Wellinghoff et al. |
| 5,041,107 A | 8/1991 | Heil, Jr. |
| 5,042,975 A | 8/1991 | Chien et al. |
| 5,147,297 A | 9/1992 | Myers et al. |
| 5,167,625 A | 12/1992 | Jacobsen et al. |

(Continued)

FOREIGN PATENT DOCUMENTS

| | | |
|---|---|---|
| JP | 58135808 A | 8/1983 |
| WO | WO 86/56488 | 11/1986 |

(Continued)

OTHER PUBLICATIONS

PCT/US2005/031501—International Search Report and Written Opinion of the ISA, dated Jan. 24, 2006.

(Continued)

*Primary Examiner* — Victoria P Shumate
(74) *Attorney, Agent, or Firm* — Sutherland Asbill & Brennan LLP

(57) ABSTRACT

Devices, such as medical devices, are provided which include a body portion having at least one reservoir which has two or more openings, the two or more openings being defined in part by a reservoir cap support; reservoir contents, such as a drug formulation or sensor, disposed inside the reservoir; and a reservoir cap which closes off the two or more reservoir openings. The reservoir cap, which can be ruptured, controls release or exposure of the reservoir contents. In one embodiment, the device is an implantable medical device and provides for the controlled release of drug or exposure of a sensor.

20 Claims, 14 Drawing Sheets

U.S. PATENT DOCUMENTS

| | | | |
|---|---|---|---|
| 5,170,801 A | 12/1992 | Casper et al. |
| 5,196,002 A | 3/1993 | Hanover et al. |
| 5,200,051 A | 4/1993 | Cozzette et al. |
| 5,202,018 A | 4/1993 | Horanyl et al. |
| 5,252,294 A | 10/1993 | Kroy et al. |
| 5,254,081 A | 10/1993 | Maurer et al. |
| 5,279,607 A | 1/1994 | Schentag et al. |
| 5,288,504 A | 2/1994 | Versic |
| 5,318,557 A | 6/1994 | Gross |
| 5,336,213 A | 8/1994 | D'Angelo et al. |
| 5,366,454 A | 11/1994 | Currie et al. |
| 5,368,588 A | 11/1994 | Bettinger et al. |
| 5,368,704 A | 11/1994 | Madou et al. |
| 5,380,272 A | 1/1995 | Gross |
| 5,387,419 A | 2/1995 | Levy et al. |
| 5,427,585 A | 6/1995 | Bettinger et al. |
| 5,429,822 A | 7/1995 | Gresser et al. |
| 5,443,508 A | 8/1995 | Giampapa |
| 5,474,527 A | 12/1995 | Bettinger et al. |
| 5,490,962 A | 2/1996 | Cima et al. |
| 5,493,177 A | 2/1996 | Muller et al. |
| 5,504,026 A | 4/1996 | Kung |
| 5,533,995 A | 7/1996 | Corish et al. |
| 5,585,069 A | 12/1996 | Zanzucchi et al. |
| 5,605,662 A | 2/1997 | Heller et al. |
| 5,662,689 A | 9/1997 | Elsberry et al. |
| 5,782,799 A | 7/1998 | Jacobsen et al. |
| 5,797,898 A | 8/1998 | Santini, Jr. et al. |
| 5,824,204 A | 10/1998 | Jerman |
| 5,842,787 A | 12/1998 | Kopf-Sill et al. |
| 5,843,767 A | 12/1998 | Beattie |
| 5,925,069 A | 7/1999 | Graves et al. |
| 5,949,187 A | 9/1999 | Xu et al. |
| 5,957,579 A | 9/1999 | Kopf-Sill et al. |
| 5,971,931 A | 10/1999 | Raff |
| 5,972,027 A | 10/1999 | Johnson |
| 5,976,101 A | 11/1999 | Sibalis |
| 5,989,445 A | 11/1999 | Wise et al. |
| 6,001,090 A | 12/1999 | Lenhart |
| 6,051,017 A | 4/2000 | Loeb et al. |
| 6,066,163 A | 5/2000 | John |
| 6,068,752 A | 5/2000 | Dubrow et al. |
| 6,081,736 A | 6/2000 | Colvin et al. |
| 6,083,763 A | 7/2000 | Balch |
| 6,096,656 A | 8/2000 | Matzke et al. |
| 6,114,658 A | 9/2000 | Roth et al. |
| 6,123,861 A | 9/2000 | Santini, Jr. et al. |
| 6,129,685 A | 10/2000 | Howard, III |
| 6,161,047 A | 12/2000 | King et al. |
| 6,171,850 B1 | 1/2001 | Nagle et al. |
| 6,178,349 B1 | 1/2001 | Kieval |
| 6,185,455 B1 | 2/2001 | Loeb et al. |
| 6,214,032 B1 | 4/2001 | Loeb et al. |
| 6,221,024 B1 | 4/2001 | Miesel |
| 6,232,150 B1 | 5/2001 | Lin et al. |
| 6,237,398 B1 | 5/2001 | Porat |
| 6,243,608 B1 | 6/2001 | Pauly et al. |
| 6,261,584 B1 | 7/2001 | Peery et al. |
| 6,264,990 B1 | 7/2001 | Knepp et al. |
| 6,289,237 B1 | 9/2001 | Mickle et al. |
| 6,306,420 B1 | 10/2001 | Cheikh |
| 6,319,241 B1 | 11/2001 | King et al. |
| 6,349,232 B1 | 2/2002 | Gordon |
| 6,366,794 B1 | 4/2002 | Moussy et al. |
| 6,384,353 B1 | 5/2002 | Huang et al. |
| 6,436,853 B2 | 8/2002 | Lin et al. |
| 6,480,730 B2 | 11/2002 | Darrow et al. |
| 6,491,666 B1 | 12/2002 | Santini, Jr. et al. |
| 6,497,729 B1 | 12/2002 | Moussy et al. |
| 6,498,043 B1 | 12/2002 | Schulman |
| 6,527,762 B1 | 3/2003 | Santini, Jr. et al. |
| 6,537,250 B1 | 3/2003 | Kriesel |
| 6,537,256 B2 | 3/2003 | Santini, Jr. et al. |
| 6,551,838 B2 | 4/2003 | Santini, Jr. et al. |
| 6,558,321 B1 | 5/2003 | Burd et al. |
| 6,571,125 B2 | 5/2003 | Thompson |
| 6,587,719 B1 | 7/2003 | Barrett et al. |
| 6,656,162 B2 | 12/2003 | Santini, Jr. et al. |
| 6,663,615 B1 | 12/2003 | Madou et al. |
| 6,669,683 B2 | 12/2003 | Santini, Jr. et al. |
| 6,702,857 B2 | 3/2004 | Brauker et al. |
| 6,730,072 B2 | 5/2004 | Schawgo et al. |
| 6,733,485 B1 | 5/2004 | Whitehurst et al. |
| 6,741,877 B1 | 5/2004 | Schults et al. |
| 6,757,560 B1 | 6/2004 | Fischer et al. |
| 6,773,429 B2 | 8/2004 | Sheppard, Jr. et al. |
| 6,797,898 B2 | 9/2004 | Heinze |
| 6,808,522 B2 | 10/2004 | Richards et al. |
| 6,809,507 B2 | 10/2004 | Morgan et al. |
| 6,827,250 B2 | 12/2004 | Uhland et al. |
| 6,849,463 B2 | 2/2005 | Santini, Jr. et al. |
| 6,890,300 B2 | 5/2005 | Lloyd |
| 6,908,770 B1 | 6/2005 | McDevitt et al. |
| 6,968,743 B2 | 11/2005 | Rich et al. |
| 7,010,345 B2 | 3/2006 | Hill et al. |
| 7,070,590 B1 | 7/2006 | Santini, Jr. et al. |
| 7,291,497 B2 | 11/2007 | Holmes et al. |
| 2001/0053885 A1 | 12/2001 | Gielen et al. |
| 2001/0056255 A1 | 12/2001 | Kost |
| 2002/0022826 A1 | 2/2002 | Reynolds et al. |
| 2002/0038137 A1 | 3/2002 | Stein |
| 2002/0055761 A1 | 5/2002 | Mann et al. |
| 2002/0072784 A1 | 6/2002 | Sheppard, Jr. et al. |
| 2002/0082527 A1 | 6/2002 | Liu |
| 2002/0082665 A1 | 6/2002 | Haller et al. |
| 2002/0099359 A1 | 7/2002 | Santini, Jr. et al. |
| 2002/0107553 A1 | 8/2002 | Hill et al. |
| 2002/0111601 A1 | 8/2002 | Thompson |
| 2002/0119176 A1 | 8/2002 | Greenberg et al. |
| 2002/0143369 A1 | 10/2002 | Hill et al. |
| 2002/0144548 A1 | 10/2002 | Cohn et al. |
| 2002/0161352 A1 | 10/2002 | Lin et al. |
| 2002/0165586 A1 | 11/2002 | Hill et al. |
| 2002/0183721 A1 | 12/2002 | Santini, Jr. et al. |
| 2002/0187260 A1 | 12/2002 | Sheppard, Jr. et al. |
| 2003/0004549 A1 | 1/2003 | Hill et al. |
| 2003/0049865 A1* | 3/2003 | Santini et al. ............... 436/518 |
| 2003/0069560 A1 | 4/2003 | Adamis et al. |
| 2003/0104590 A1* | 6/2003 | Santini et al. ............... 435/174 |
| 2003/0105455 A1 | 6/2003 | Santini, Jr. et al. |
| 2003/0176854 A1 | 9/2003 | Rodstrom |
| 2004/0043042 A1 | 3/2004 | Johnson et al. |
| 2004/0082937 A1 | 4/2004 | Ausiello et al. |
| 2004/0106914 A1 | 6/2004 | Coppeta et al. |
| 2004/0106953 A1 | 6/2004 | Yomtov et al. |
| 2004/0121486 A1 | 6/2004 | Uhland et al. |
| 2004/0127942 A1 | 7/2004 | Santini, Jr. et al. |
| 2004/0143236 A1 | 7/2004 | Santini, Jr. et al. |
| 2004/0166140 A1 | 8/2004 | Santini, Jr. et al. |
| 2004/0247671 A1 | 12/2004 | Prescott et al. |
| 2005/0005676 A1 | 1/2005 | Crawley |
| 2005/0050859 A1 | 3/2005 | Coppeta et al. |
| 2005/0055014 A1 | 3/2005 | Coppeta et al. |
| 2005/0077584 A1 | 4/2005 | Polito et al. |
| 2005/0096587 A1 | 5/2005 | Santini, Jr. et al. |
| 2005/0100937 A1 | 5/2005 | Holmes |
| 2005/0143715 A1 | 6/2005 | Santini, Jr. et al. |
| 2006/0076236 A1 | 4/2006 | Shah et al. |
| 2006/0171989 A1 | 8/2006 | Prescott et al. |

FOREIGN PATENT DOCUMENTS

| | | |
|---|---|---|
| WO | WO 93/03790 A1 | 3/1993 |
| WO | WO 99/03684 A2 | 3/1993 |
| WO | WO 98/26814 A1 | 6/1998 |
| WO | WO 01/28629 A1 | 4/2001 |
| WO | WO 01/37926 A1 | 5/2001 |
| WO | WO 01/88525 A1 | 5/2001 |
| WO | WO 02/056862 A1 | 7/2002 |
| WO | WO 02/058678 A2 | 8/2002 |
| WO | WO 03/024355 A1 | 3/2003 |

OTHER PUBLICATIONS

PCT/US2005/031501—International Preliminary Report on Patentability, dated Nov. 6, 2006.

Amendment and Response to Office Action filed Jul. 31, 2008 in U.S. Appl. No. 11/339,062.

Notice of Allowance mailed Dec. 2, 2008 in U.S. Appl. No. 11/339,062.

Reynaerts et al., "An implantable drug-delivery system based on shape memory alloy micro-actuation," Sensors and Actuators, A 61:455-462 (1997).

Peterman et al., "Localized chemical release from an artificial synapse chip," PNAS 101(27):9951-9954 (2004).

* cited by examiner

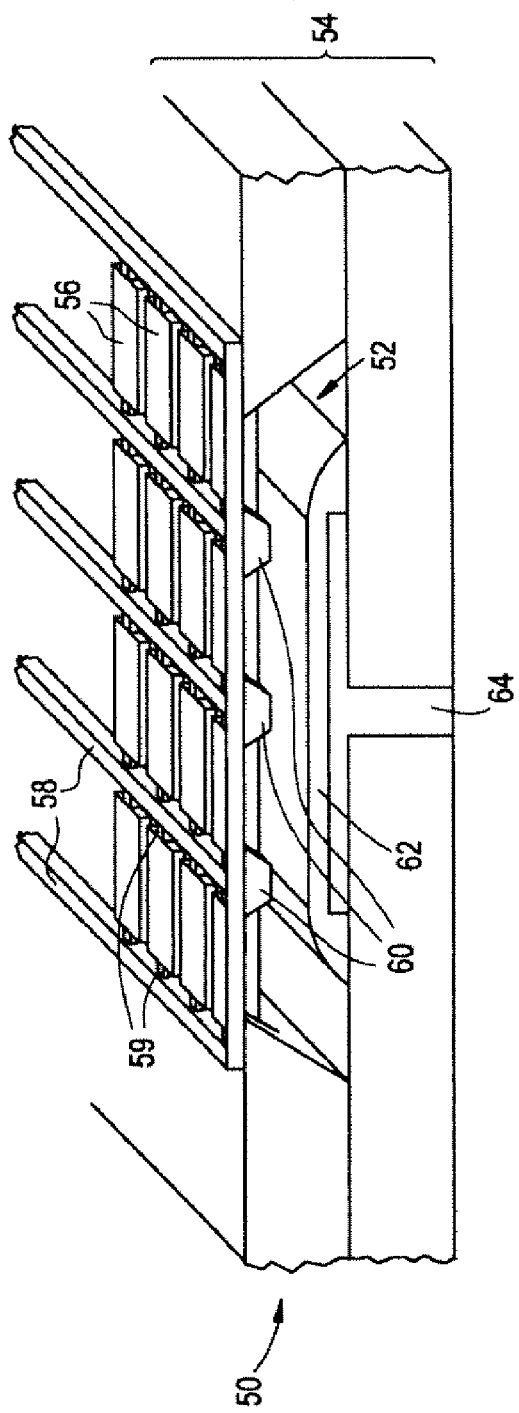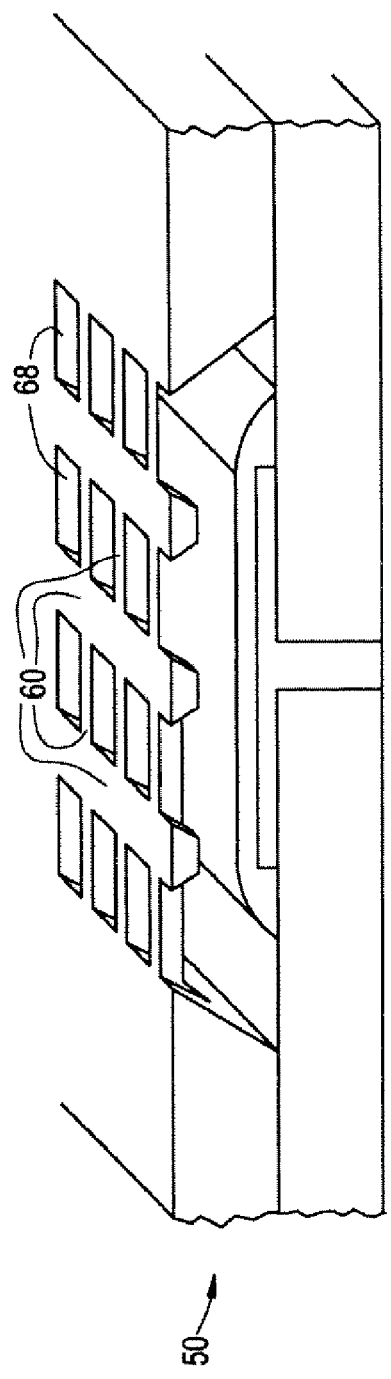

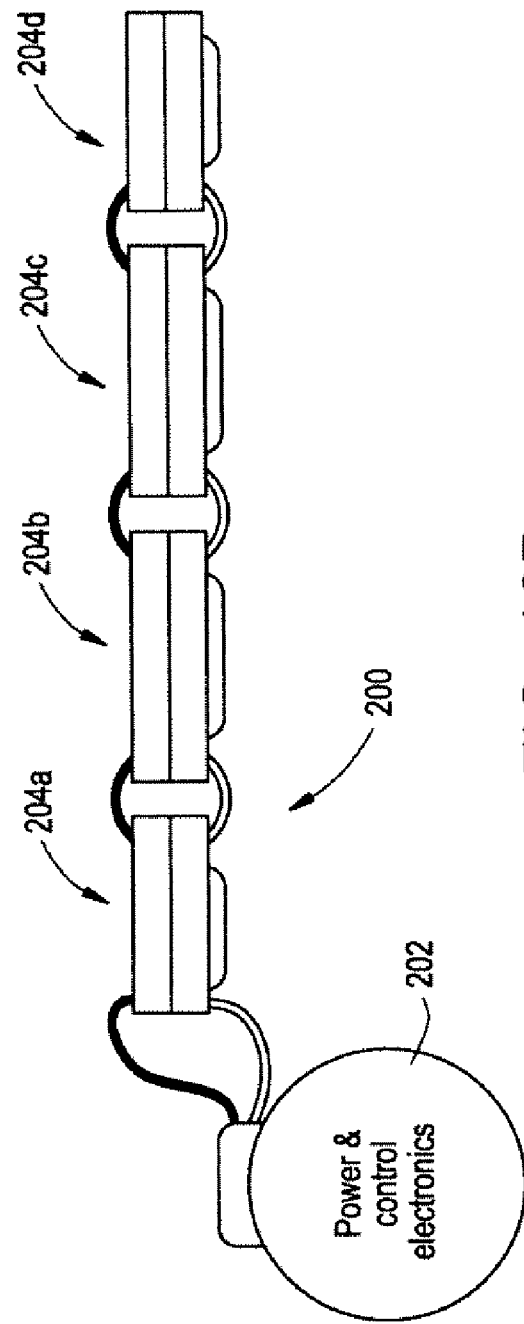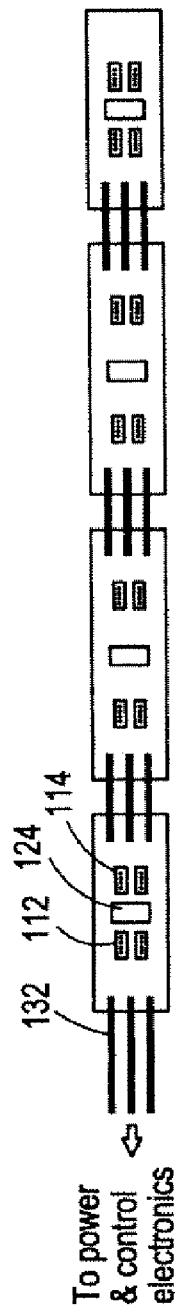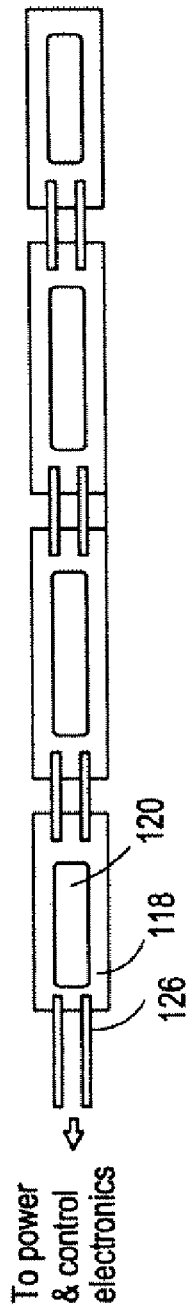

MULTI-OPENING RESERVOIR DEVICES FOR CONTROLLED RELEASE OR EXPOSURE OF RESERVOIR CONTENTS

CROSS-REFERENCE TO RELATED APPLICATIONS

This is a continuation of U.S. application Ser. No. 11/217,799, filed Sep. 1, 2005, which claims the benefit of U.S. Provisional Application No. 60/606,387, filed Sep. 1, 2004. The applications are incorporated herein by reference in their entirety.

BACKGROUND OF THE INVENTION

This invention is generally in the field of devices and methods for controlled exposure or release of reservoirs contents.

U.S. Pat. No. 5,797,898, U.S. Pat. No. 6,527,762, U.S. Pat. No. 6,491,666, and U.S. Pat. No. 6,551,838, and U.S. Patent Application Publication No. 2004/0121486, describe devices for the controlled release or exposure of reservoir contents. The devices include a plurality of reservoirs in which contents are isolated until the time selected for release or exposure. For example, the reservoirs can contain a drug formulation for controlled release or sensors for exposure. In several embodiments, each reservoir has a discrete reservoir cap closing off a reservoir opening, and the device includes means for disintegrating or permeabilizing the reservoir cap, for example by electrochemical oxidation or electrothermal ablation.

Reservoir caps generally are self-supporting depending upon the size of the reservoir opening across which they span, i.e., the reservoir opening can be small enough so that the center of the reservoir cap does not require structural support in addition to the support from the substrate edges defining the reservoir opening and the substrate surface surrounding the opening ("streets") upon which the reservoir caps are secured. However, in many applications—for example to expose a larger sensor area and/or to increase the rate of mass transport of molecules into and/or out of the reservoir—it would be desirable to be able to increase the area of the reservoir opening beyond that which a reservoir cap of certain materials and thickness could support itself. It also would be desirable to provide a device with reservoir caps able to withstand stresses placed upon the reservoir cap in the device's intended application, as certain membranes, while self supporting, nevertheless could be easily torn or fractured by normal application stresses. It would also be desirable to provide, in some instances, a reservoir device having at least one wide, shallow reservoir that can utilize reservoir cap-based techniques for active, controlled reservoir opening.

SUMMARY OF THE INVENTION

Reservoir-based devices are provided in which an individual reservoir has at least two openings with a support structure therebetween and closed by reservoir caps covering the openings to control release or exposure of reservoir contents. In one aspect, a device is provided for the controlled release or exposure of reservoir contents, which includes a substrate; at least one reservoir disposed in the substrate, the reservoir having two or more openings; reservoir contents located in the reservoir; two or more discrete reservoir caps, each reservoir cap sealingly covering at least one of the reservoir openings; and control means for selectively disintegrating or permeabilizing the reservoir caps. In one embodiment, the two or more openings are on the same surface or side of the substrate. In one embodiment, the substrate comprises at least one reservoir cap support extending over the reservoir contents, wherein the two or more reservoir caps are in part supported by the at least one reservoir cap support. In one embodiment, the substrate has two or more substrate portions bonded together, and one of the substrate portions includes the reservoir cap support. The reservoir cap support may be made from a coating or deposited material distinct from the substrate. In one embodiment, the substrate comprises an array of two or more of the reservoirs.

In one embodiment, the reservoirs caps can be individually disintegrated or permeabilized. The reservoir caps covering a selected reservoir may be disintegrated substantially simultaneously, or the reservoir caps covering a selected reservoir may be disintegrated serially. In one embodiment, two or more of the reservoir caps are in electrical communication and are operable to disintegrate substantially simultaneously upon application of an electrical current.

In one embodiment, the reservoir is a micro-reservoir. In one embodiment, the reservoir comprises three or more reservoir openings and corresponding reservoir caps. In a preferred embodiment, the reservoir caps comprise a metal film. In one embodiment, the reservoir cap comprises a metal selected from gold, platinum, titanium, tin, and alloys and other combinations thereof.

In one embodiment, the control means disintegrates the reservoir cap, e.g., by a process that includes electrothermal ablation. In a preferred embodiment, the reservoir caps comprise an electrically conductive material, and the device further includes an electrical input lead and an electrical output lead, which are connected to the reservoir caps such that upon application of an electrical current through the reservoir caps, via the input leads and output leads, the reservoir caps are disintegrated to release or expose the reservoir contents. In various embodiments, the reservoir cap disintegration comprises a chemical reaction, dissolution, biodegradation, mechanical rupture, a phase change, or a combination thereof.

In a preferred embodiment, the reservoir contents comprises a sensor or a component thereof. In another embodiment, the reservoir contents comprises a drug.

In one embodiment, the device further includes actuation electronics and a power source, wherein the device is packaged for implantation into a human or animal patient.

In another aspect, methods are provided for the controlled delivery of molecules. In one embodiment, the method includes the steps of positioning at a preselected location the multi-cap device described herein, wherein the reservoir contents comprise chemical molecules for delivery; and controlling the diffusion through or disintegration of the reservoir caps to enable the molecules to pass outward from the device to the preselected location.

In still another aspect, methods are provided for the controlled exposure of an immobilized reagent or a secondary device. In one embodiment, the method includes the steps of positioning at a preselected location the multi-cap device described herein, wherein the reservoir contents comprise an immobilized reagent, a secondary device, or a combination thereof, and controlling the disintegration of the reservoir caps to expose the reservoir contents to the environment at the preselected location.

In yet another aspect, methods are provided for making the devices described herein. In exemplary embodiments, the fabrication methods include a boron doping method or a DRIE method.

BRIEF DESCRIPTION OF THE FIGURES

FIGS. 5A-B are cross-sectional perspective views one embodiment of a multi-cap reservoir device, shown with (FIG. 5A) and without (FIG. 5B) electrically conductive reservoir caps, and associated traces and leads, covering the multiple openings of the single reservoir.

FIG. 6A is a cross-sectional view of a slice of the device taken at line A-A' shown in top view (FIG. 6B) of the device. FIG. 6C is a bottom view of the device.

FIG. 7A is a cross-sectional view of a slice of the device taken at line A-A' shown in top view (FIG. 7B) of the device. FIG. 7C is a bottom view of the device.

FIG. 8A is a cross-sectional view of a slice of the device taken at line A-A' shown in top view (FIG. 8B) of the device. FIG. 8C is a bottom view of the device.

FIG. 9A is a cross-sectional view of a slice of the device taken at line A-A' shown in top view (FIG. 9B) of the device. FIG. 9C is a bottom view of the device.

FIGS. 10A-C illustrate one embodiment of a sensor device having power and control electronics module connected to a separate chain of flexibly connected, multi-cap reservoir-based sensor units. FIG. 10A is a side view, FIG. 10B is a top view (with bottom electrical connections not shown), and FIG. 10C is a bottom view (with top electrical connections not shown).

DETAILED DESCRIPTION OF THE INVENTION

Figure 1:
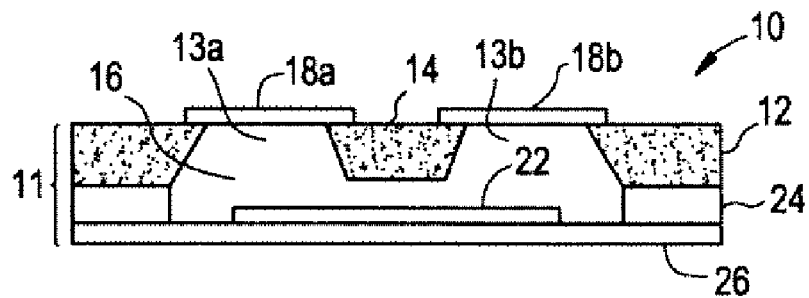
FIG. 1 is a cross-sectional view of one embodiment of a multi-cap reservoir device.

Reservoir containment devices have been developed that include at least one reservoir having two or more openings, typically adjacent to one another, e.g., in an array, wherein the reservoir openings are covered by discrete reservoir caps. Each reservoir cap can be independently and separately disintegrated or groups of the reservoir caps can be actuated simultaneously. For instance, the two or more reservoir caps covering a single reservoir can, temporally speaking, be actuated simultaneously or serially to uncover the two or more openings. These multiple openings can effectively and advantageously act like a single larger opening (from a mass transport perspective), yet permit the effective opening size to be covered by a selectively removable/openable structure that is self-supporting across the opening.

Simultaneous actuation can be obtained in two distinct ways: In one case, two or more caps are not in electrical connection; however, an electrical current is sent through two reservoir caps independently but at the same time. In another case, two or more caps are electrically connected and are actuated by a single application of electrical current.

A support structure, a reservoir cap support, is disposed under the reservoir caps, in or over the reservoir, to support the reservoir caps in part. The openings of the reservoir are defined, in part, by a support structure disposed under and supporting the outer edge part of the reservoir caps. These devices and opening systems are for controlled opening of sealed reservoirs (preferably hermetically sealed) to selectively release or expose reservoir contents, such as drug formulations or sensors, isolated therein. In alternative embodiments, the support structure is located outside of the reservoir or support structures are located both inside and outside of the reservoir.

As used herein, the term "disintegrate" is used broadly to include without limitation degrading, dissolving, rupturing, fracturing or some other form of mechanical failure, as well as fracture and/or loss of structural integrity of the reservoir cap due to a chemical reaction or phase change (e.g., melting or vaporization), unless a specific one of these mechanisms is indicated. Electrothermal ablation is a preferred form of disintegration. In another embodiment, the disintegration comprises corrosion, e.g., electrochemically induced oxidation and dissolution. Representative examples of some of these disintegration techniques are described in U.S. Pat. No. 5,797,898, U.S. Pat. No. 6,527,762, and U.S. Patent Application Publication No. 2004/0121486.

As used herein, the terms "comprise," "comprising," "include," and "including" are intended to be open, non-limiting terms, unless the contrary is expressly indicated.

Illustrative Embodiments of the Multi-Cap Reservoir Devices and Systems

The myriad embodiments of devices that can be created to use the multi-cap reservoir systems and methods described herein can be understood with reference to the following non-limiting illustrations (FIGS. 1-10) and descriptions.

In one embodiment, the containment device isolates a secondary device (such as a sensor or sensing component) in each of one or more reservoirs, where each reservoir has multiple openings (two are shown) covered by discrete reservoir caps that are in part supported by a reservoir cap support structure. Optionally, the substrate defining the reservoir is a multilayer structure. In one embodiment, this multilayer substrate includes a spacer portion to increase the depth and volume of the reservoir. This spacer portion can be any structural material that bonds to the reservoir cap substrate and to another substrate material, e.g., such as one that serves as the sealing layer or secondary device substrate (which for example may depend on whether the device is a sensor device or a drug or chemical delivery device). This spacer portion could be made from a semiconductor (e.g., silicon), a polymer (e.g., an epoxy), a metal or alloy (e.g., electroplated gold), a ceramic (e.g., an oxide, nitride, or carbide of silicon or aluminum—such as aluminum oxide or alumina), or a low-temperature co-fired ceramic (LTCC), and the like.

FIG. 1 is a cross-sectional view of one embodiment of a multi-cap reservoir device. The device 10 includes a substrate 11, which comprises a first substrate portion 12, a second substrate portion (i.e., spacer) 24, and a sealing layer 26. In this case, the sealing layer also serves as a substrate for the secondary device (e.g., sensor). The three components 12, 24, and 26 are bonded together and define reservoir 16. Part of the first substrate portion serves as reservoir cap support 14 and spans the reservoir 16 (into and out of the drawing sheet in FIG. 1). The reservoir 16 has a plurality (two are shown) of openings 13a and 13b, sealed closed by reservoir caps 18a and 18b, respectively. These reservoir caps are in part supported by reservoir cap support 14 and cover the reservoir 16 to isolate secondary device 22 located therein. The secondary device 22 is secured to sealing layer 26. It is noted that in another embodiment, a separate sealing layer is not required where the bottom surface of the reservoir is integrally formed with the sidewalls, e.g., where the second substrate portion and sealing layer are unitary.

Figure 4:
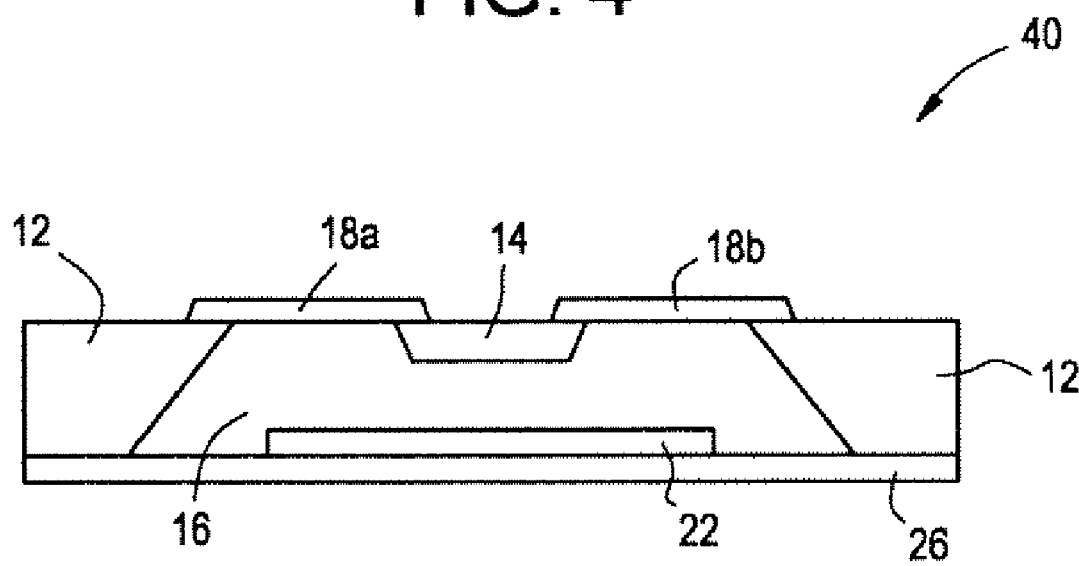
FIG. 4 is a cross-sectional view of another embodiment of a multi-cap reservoir device.

FIG. 4 is a cross-sectional view of another embodiment of a multi-cap reservoir device. The device 40 includes a substrate 12 bonded to sealing layer 26, which together define reservoir 16. Unlike FIG. 1, there is no "spacer" in this embodiment. The sealing layer also serves as a substrate for secondary device 22. The device further includes reservoir cap support 14, which spans the reservoir 16 (into and out of the drawing sheet in FIG. 4). The reservoir 16 has openings 13a and 13b, which are sealed/closed by reservoir caps 18a and 18b, respectively. These reservoir caps are in part supported by reservoir cap support 14 and cover the reservoir 16 to isolate secondary device 22 located therein.

For clarity, only one reservoir is shown in FIGS. 1 and 4; however, the device can include an array of several reservoirs, each of which has its own multiple reservoir caps. It should also be noted for clarity that the reservoir is a sealed enclosure despite any appearance to the contrary suggested by the "cut-away" cross-section view of FIGS. 1, 2A, 3, 4, and 5.

In operation, the reservoir caps 18a and 18b are permeabilized or disintegrated, serially or simultaneously by appropriate means (not shown) to open the reservoir and expose the secondary device to one or more environmental components outside the device. The multiple openings advantageously can permit more rapid diffusion and/or flow of material into and out of the reservoir than with a single opening. For instance, if the secondary device is a chemical or biological sensor, and the device is part of an implantable medical device, then the larger area for mass transport provided by the multiple openings can facilitate more rapid contact of the sensor with an analyte, which would lead to better sensing functionality of the device (e.g., shorter response times, increased sensitivity, lower limits of detection, etc.).

Figure 2A:
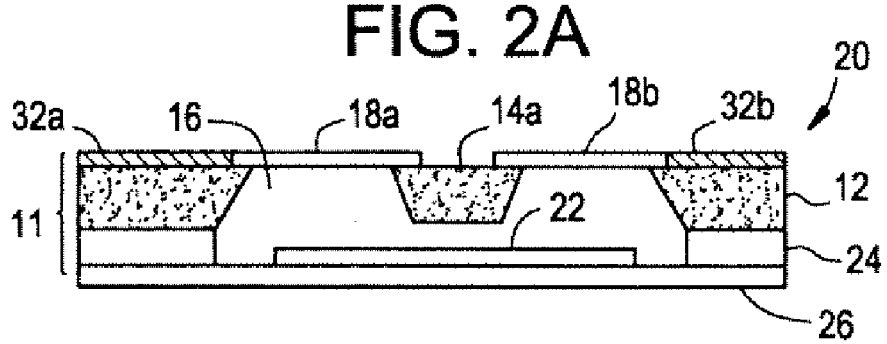
FIGS. 2A-B show a cross-sectional view (FIG. 2A) and a plan view (FIG. 2B) of one embodiment of a multi-cap reservoir device that includes reservoir caps formed of a conductive material and in electrical connection with a pair of leads for passing an electrical current effective to disintegrate the reservoir caps by electrothermal ablation.
Figure 2B:
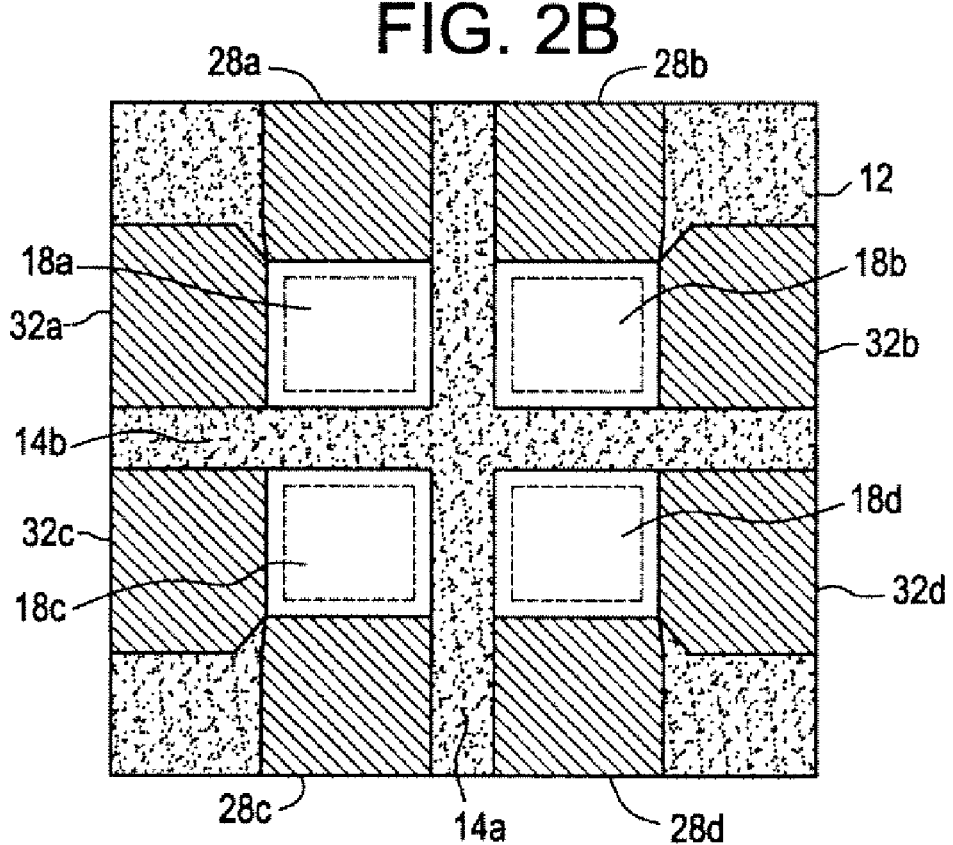

In one particular embodiment, the reservoir caps are formed of a conductive material and in electrical connection with a pair of leads for passing an electrical current effective to disintegrate the reservoir caps by electrothermal ablation, as described in U.S. Patent Application Publication No. 2004/0121486 A1 to Uhland et al., which is incorporated hereby by reference. FIGS. 2A-B show a cross-sectional view (FIG. 2A) and a plan view (FIG. 2B) of such an embodiment. The device 20 includes a substrate 11, which comprises a first substrate portion 12, a second substrate portion (i.e., spacer) 24, and a sealing layer 26. The three components 12, 24, and 26 are bonded together and define reservoir 16. Part of the first substrate portion 12 serves as reservoir cap support 14 and spans the reservoir 16. The reservoir 16 has a plurality (four are shown in FIG. 2B) of openings sealed closed by reservoir caps 18a, 18b, 18c, and 18d. The reservoir caps are in part supported by reservoir cap supports 14a and 14b and cover the reservoir 16 to isolate secondary device 22 located therein. The secondary device 22 is secured to sealing layer 26. On the surface of substrate portion 12, reservoir caps 18a, 18b, 18c, and 18d are electrically connected, respectively, to input lead and output lead pairs 28a/32a, 28b/32b, 28c/32c, and 28d/32d. The leads are connected to a source of electric power (not shown) for applying an electrical current through each of the reservoir caps. In one embodiment, the source of electrical current is a capacitor that is charged locally by an on-board battery or remotely by an RF signal.

In operation, the reservoir caps 18a, 18b, 18c, and 18d are disintegrated, serially or simultaneously, by electrothermal ablation to open the reservoir and expose the secondary device to one or more environmental components outside the device. As can be understood from the foregoing description and FIGS. 2A-B, the four reservoir caps each cover roughly a quarter of the total area available for material to pass into and/or out of the reservoir. This opening system thus provides greater flexibility for controlling the transport rate and permits the use of larger reservoirs with larger effective openings with reservoir caps that have a construction and dimensions that could not be self-supporting. It also can provide reservoir cap(s) able to withstand stresses greater than its own weight, as well as normal or expected stresses incurred in the device's intended application.

Figure 3:
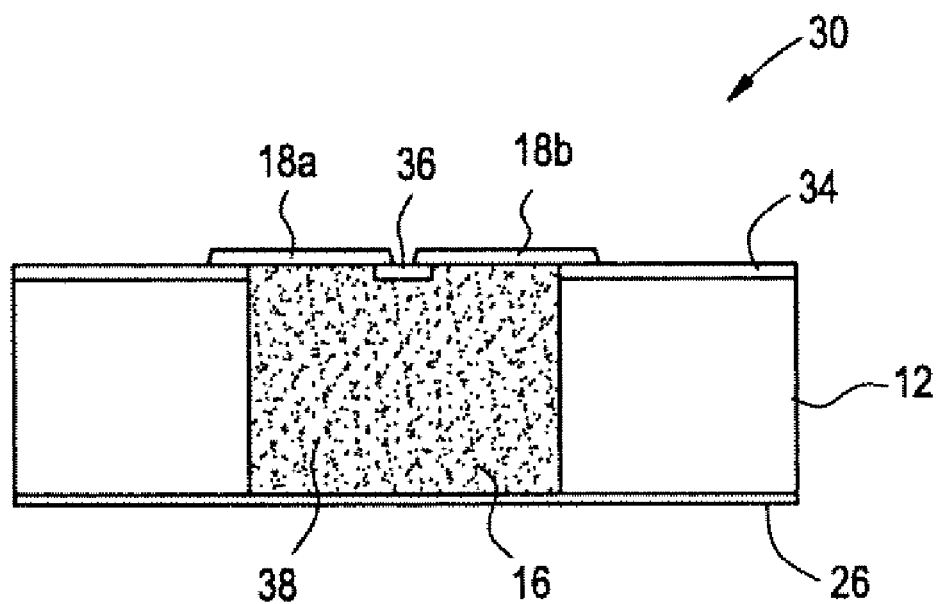
FIG. 3 is a cross-sectional view of one embodiment of a multi-cap reservoir device in which the reservoir cap support is made from a coating or deposited material that is distinct from the substrate or that is a very thin layer of a multilayer substrate.

In another embodiment, the reservoir cap support is made from a coating or deposited material that is distinct from the substrate, or that is a very thin layer of a multilayer substrate. FIG. 3 is a cross-sectional view of one such embodiment. The device 30 includes a substrate 12 and sealing layer 26, which together essentially define reservoir 16. The reservoir 16 has a plurality (two are shown) of openings, which are sealed closed by reservoir caps 18a and 18b. The reservoir caps are supported by coating layer 34, which includes reservoir cap support 36. A drug formulation 38 is loaded in and isolated inside reservoir 16 until the reservoir caps are actuated (e.g., disintegrated or permeabilized).

FIGS. 5A and 5B show a cross-sectional, perspective view of a device 50 having a reservoir 52 in substrate 54 containing a sensor 62. The sensor is electrically connected (data and power transmission) through via 64. The reservoir has sixteen openings 68 (in a 4×4 array) defined by support structures 60. In FIG. 5A, the openings are covered by reservoir caps 56, which are electrically connected by conductive traces 58 with input and output leads 59 through the reservoir caps. In FIG. 5B, the reservoir caps and traces are not shown in order to more clearly show the openings in the support structure under the reservoir caps.

In FIG. 1, the support structure is a portion of the substrate or is fabricated out of (a portion of) the substrate. In such a case, the material of the substrate and the support structure are the same and integrally connected/formed, because at one point in the fabrication process the support structure and the substrate were indistinguishable. By contrast, in FIG. 3, the support structure and the substrate are different, either in the sense that they have different composition (i.e., are formed from different materials) or in the sense that they have the same composition but are created in distinct steps/different methods. For instance, a silicon substrate could be grown from a single crystal and a silicon support structure could be deposited using various deposition methods. The support material can be deposited using a range of methods known in the art, including microfabrication/micromachining methods such as plasma sputtering, e-beam evaporation, ion-beam sputtering or evaporation, various chemical vapor deposition (low pressure or plasma-enhanced) methods, and spin coating (spin-on glass or various polymers). Such support layers also could be grown thermally, such as the growth of a thick silicon oxide layer on silicon. In any of these methods, the "deposited" layer is patterned in some way to create the support structure.

In various preferred embodiments shown in FIGS. 6-10 (where like parts have like numbering), the reservoir contents comprise a sensor, particularly a glucose sensor. In some of these embodiments, the device includes at least two substrate portions: a sensor portion (including the sensor electrodes and, e.g., associated catalysts/reagents and selectively permeable membranes) and a reservoir portion (including the openable reservoir openings, the reservoir caps, and means for disintegrating the reservoir caps). These portions may be separately fabricated and then bonded together as part of the ultimate device.

Figure 6A:
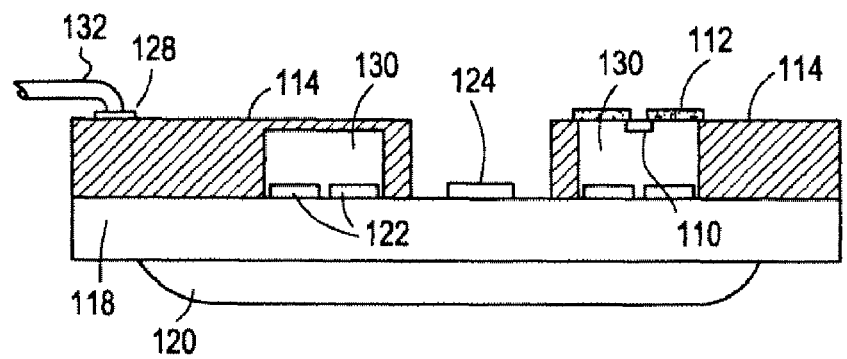
FIGS. 6A-C illustrate one embodiment of a multi-cap reservoir device containing sensors in the reservoirs with a reference electrode mounted on the sensor substrate portion between separate reservoir substrates.
Figure 6B:
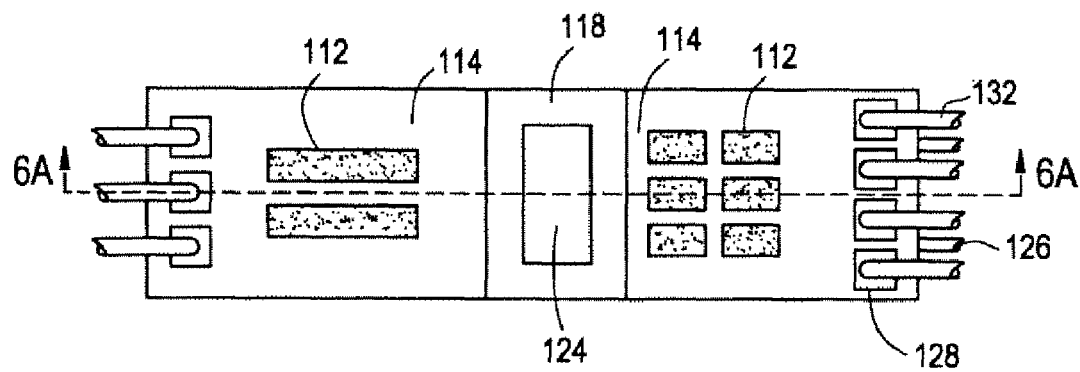
Figure 6C:
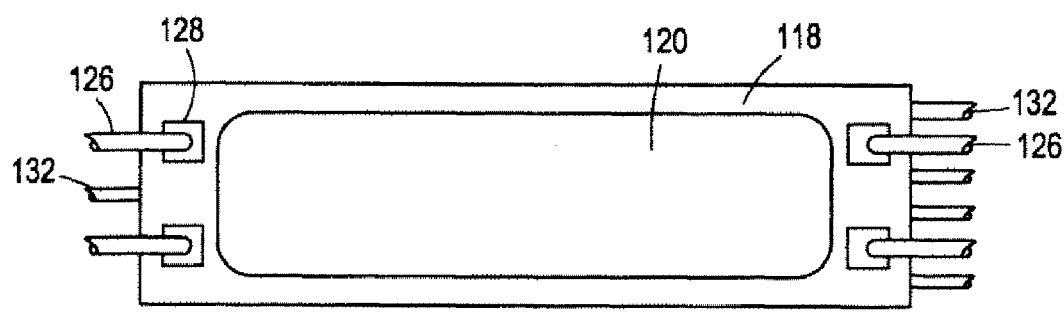

In one embodiment, shown in FIGS. 6A-C, the multi-cap reservoir device includes reservoir substrate portions 114, reservoirs 130, reservoir caps 112, support structures 110, sensor substrate portion 118, sensor electrodes 122, reference electrode 124, metal can 120 containing sensor electronics, bond pads 128, wires 132 for relaying power (current) to the reservoir cap side of the device, and wires 126 for relaying power and data to and from the sensor side of the device. (For clarity of illustration, electrical traces to/from each reservoir cap and bond pads have been omitted from the Figures.) In this embodiment, the reference electrode is mounted on the sensor substrate portion between separate reservoir substrates.

In this embodiment of FIG. 6, there is one reservoir per reservoir substrate. In other embodiments, there may be two, three, or more, reservoirs per reservoir substrate. In yet other embodiments, vias may be used to electrically connect components of the reservoir substrate portion and components of the sensor substrate portion of the device, which may, for example, allow fewer electrical leads between the device and separate (e.g., distal or external) controllers/power sources. FIG. 6B also illustrates that different numbers and shapes of reservoir openings and reservoir caps may be used (e.g., compare left side reservoir with right side reservoir).

Figure 7A:
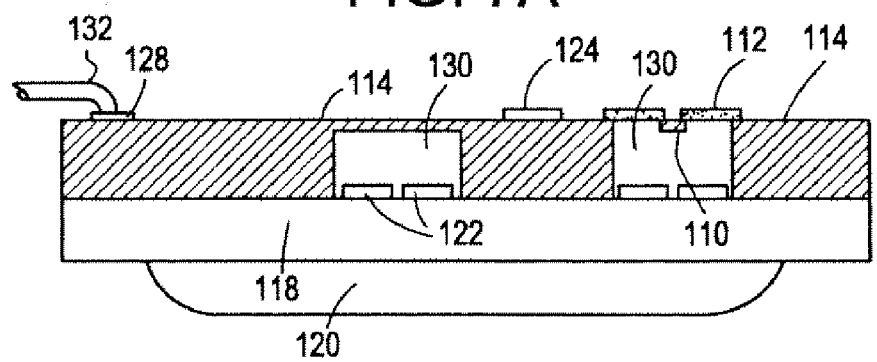
FIGS. 7A-C illustrate one embodiment of a multi-cap reservoir device containing sensors in the reservoirs with a reference electrode mounted on the reservoir substrate portion between reservoirs.
Figure 7B:
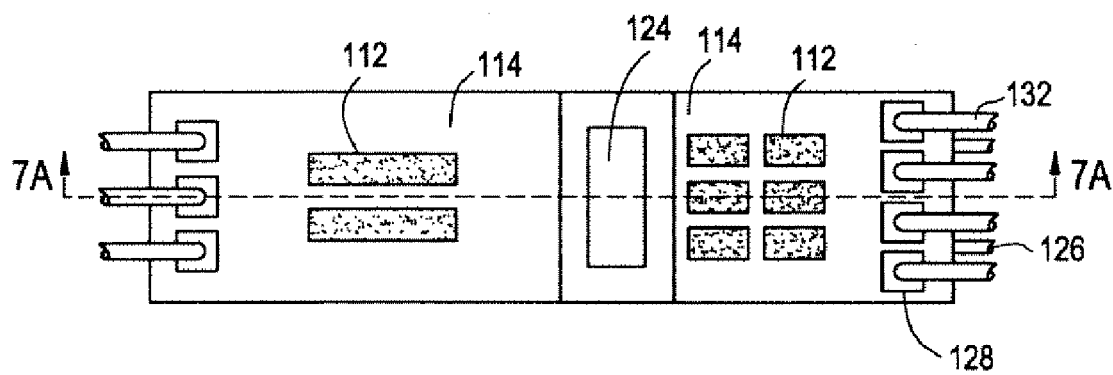
Figure 7C:
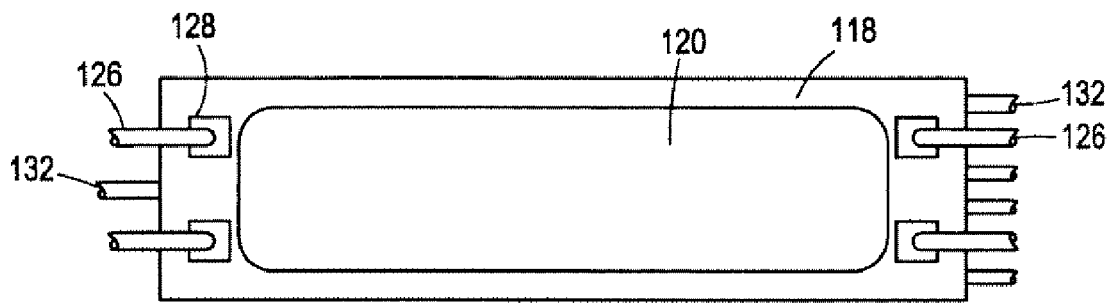
Figure 8A:
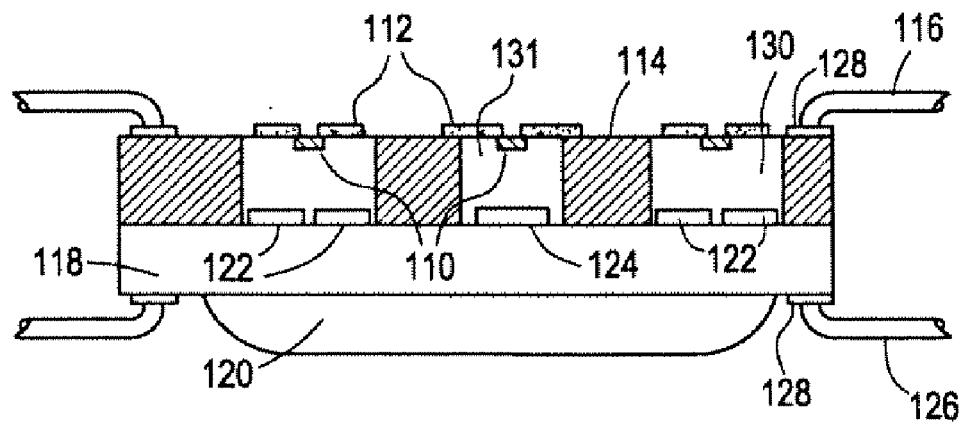
FIGS. 8A-C illustrate one embodiment of a multi-cap reservoir device containing sensors in the reservoirs with a reference electrode mounted on the sensor substrate and disposed in its own separate reservoir covered by reservoir caps.
Figure 8B:
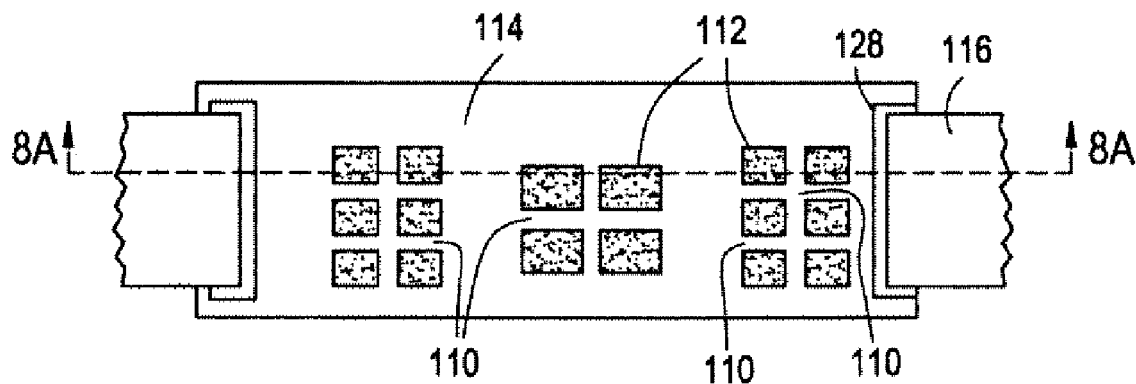
Figure 8C:
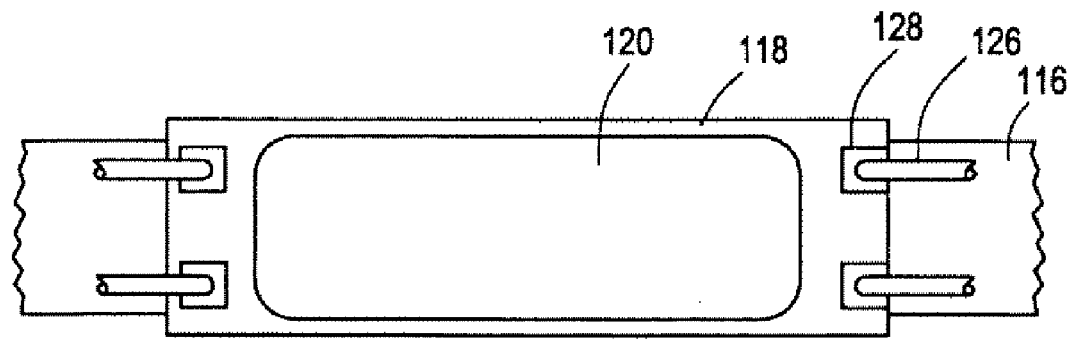
Figure 9A:
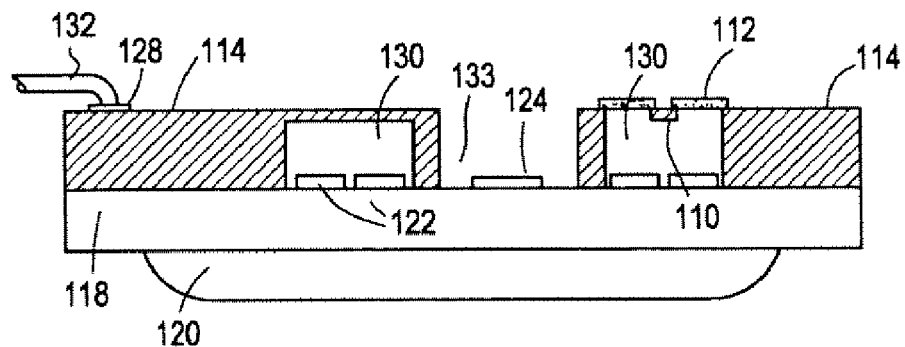
FIGS. 9A-C illustrate one embodiment of a multi-cap reservoir device containing sensors in the reservoirs with a reference electrode mounted on the sensor substrate portion disposed in a hole with the reservoir substrate between two capped reservoirs.
Figure 9B:
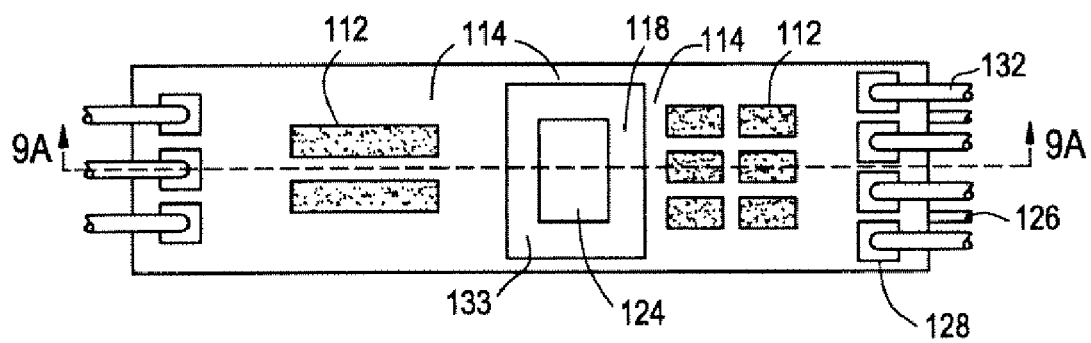
Figure 9C:
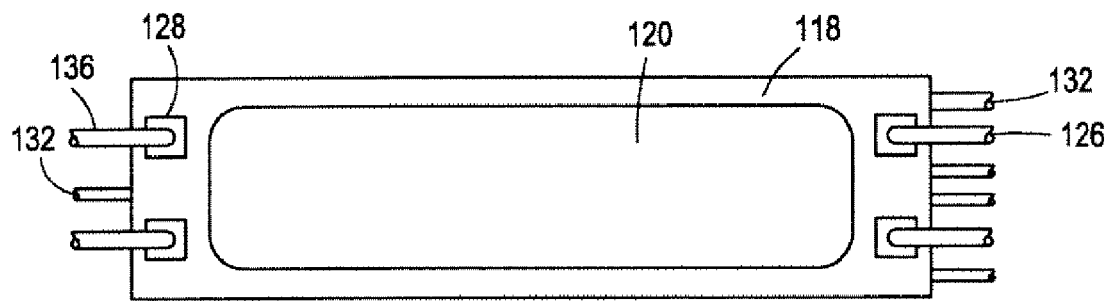

Another variation of a sensor device is shown in FIGS. 7A-C. It is like that of FIG. 6; however, the reference electrode 124 is mounted on the reservoir substrate portion 114 between reservoirs, rather than on the sensor substrate portion 118, and there is a single reservoir substrate portion which has the two reservoirs shown. Yet another variation of a sensor device is shown in FIGS. 8A-C. It is similar to that of FIGS. 6 and 7; however, the reference electrode 124 is disposed in its own separate reservoir 131 covered by reservoir caps 112 and a ribbon cable 116 is used in place of discrete wires 126. In still another embodiment, shown in FIGS. 9A-C, the reference electrode 124 is mounted on the sensor substrate portion disposed in a hole 133 in the substrate portion 114 with the reservoir substrate between the two capped reservoirs.

In some embodiments, the device includes an array of multi-cap reservoir components that are flexibly connected together. Examples of devices comprising flexibly connected components are described in U.S. Patent Application Publication No. 2002/0099359 and in U.S. Pat. No. 6,498,043, which are incorporated herein by reference. One example of a sensor device is illustrated in FIGS. 10A-C. Device 200 includes a power and control electronics module 202 connected to a separate chain of flexibly connected, multi-cap reservoir-based sensor units 204a-d. The units can be flexibly connected by wires and/or an outer sheath (e.g., one made of a biocompatible elastomer or polymer), among other techniques.

The multi-cap reservoir systems and devices described herein can be used with or incorporated into a variety of devices, including implantable medical devices and other devices. Examples include drug delivery devices, diagnostic and sensing devices, some of which are described in U.S. Pat. No. 5,797,898, U.S. Pat. No. 6,551,838, U.S. Pat. No. 6,527,762, as well as in U.S. Patent Application Publications No. 2002/0099359, No. 2003/0010808, No. 2004/0121486, which are incorporated herein by reference. In some embodiments, the multi-cap reservoir device/system described herein is a subcomponent of another device. For example, it may be part of an implantable drug delivery device that further comprises a sensor indicative of a physiological condition of a patient, an electrode for providing electrical stimulation to the body of a patient, a pump, a catheter, or a combination thereof. Examples of some of these are described in U.S. Patent Application Publications No. 2004/0127942 A1 and No. 2004/0106953 A1, and in U.S. Pat. No. 6,491,666, which are incorporated herein by reference.

Further Details of the Multi-Cap Reservoir Devices and Systems

Various advantages arise from reservoir cap supports positioned over a reservoir so that multiple reservoir caps smaller than the reservoir opening can be combined to separate the contents of a reservoir from the environment outside of the reservoir. First, larger reservoirs can be formed, as any structural limitations stemming from large reservoir caps are eliminated (e.g., lack of structural integrity due to lack of structural support). Secondly, for reservoir contents which include secondary devices, the area of transport to/from the secondary device and the sensor area upon permeabilization or disintegration of the multiple reservoir caps is increased due to the larger reservoir. Thirdly, for reservoir contents that include molecules for release, the rate of release upon permeabilization or disintegration of the multiple reservoir caps is increased because of the multiple reservoir openings. Additionally, the multi-cap reservoir, which can be larger, allows for more molecules for release and larger secondary devices within the reservoir.

To illustrate another advantage of the devices and methods described herein, one can consider a device designed to open using electrothermal ablation and having a large area of reservoir opening. If a self-supporting reservoir cap were desired, then one might tend to design the reservoir cap to have an increased thickness in order to provide the necessary mechanical integrity in the absence of additional support structures. However, by increasing the thickness of the reservoir cap, one would be decreasing the efficiency of the actuation method because more electrical current would be required as compared to a thinner reservoir cap. Accordingly, it would be advantageous to provide multiple smaller, lower current fuses covering a single reservoir than it would be to have a larger single higher current reservoir cap even if that reservoir cap could be made to mechanically support itself. Given the need to encapsulate comparatively larger volume reservoir contents for subsequent release or exposure, tradeoffs may be required among the strength of the reservoir cap, the number and size of the disintegratable reservoir caps, and the complexity of the means for disintegrating the reservoir caps. In addition, a larger opening can provide a correspondingly larger exposed surface area, which may be a particularly important variable for sensors, especially planar sensors. In such cases, the volume of reservoir optionally may desirably be quite small. For example, a thinner substrate may be used to reduce the distance over which molecules must travel from outside of the reservoir (e.g., in the body) to the surface of the sensor. In contrast, for a non-planar sensor (e.g., one similar to THERASENSE's wire-based glucose sensor) the three-dimensional character of the sensor may render the volume of the reservoir as equally important as the surface area exposed.

Serial actuation can be obtained by keeping the reservoir caps electrically separated and then actuating them independently, one after another. In another embodiment, the reservoir caps can be electrically connected in series to get simultaneous actuation from a single current application. Essentially any combination of simultaneous and serial actuation can be achieved, depending on how the reservoir caps are electrically wired together and how the current is applied. Generally in the thermal ablation embodiments, when reservoir caps are connected in parallel, the electrical currents may differ due to voltage drop along the traces. The reservoir caps closest to the bond pads will have the largest current and will disintegrate sooner (at least on a microsecond time scale) than one further away. The parallel connection typically is preferred, because the disintegration of any one reservoir cap will not affect that of another. With a series electrical connection, while the current is identical, there may be differences in the reservoir cap properties that may cause one to disintegrate slightly faster than another. The disintegration of the first reservoir cap increases the circuit resistance and causes a drop in the current through the remaining caps.

Substrate and Reservoirs

In one embodiment, the containment device comprises a body portion, i.e., a substrate, that includes one or more reservoirs for containing reservoir contents sealed in a fluid tight or hermetic manner. As used herein, the term "hermetic" refers to a seal/containment effective to keep out helium, water vapor, and other gases. As used herein, the term "fluid tight" refers to a seal/containment which is not gas hermetic, but which are effective to keep out dissolved materials (e.g., glucose) in a liquid phase. The substrate can be the structural body (e.g., part of a device) in which the reservoirs are formed, e.g., it contains the etched, machined, or molded reservoirs. A reservoir is a well, a container, or a cavity. In a one embodiment, the device includes a plurality of the reservoirs located in discrete positions across at least one surface of the body portion. In another embodiment, there is a single reservoir per each reservoir substrate portion; optionally two or more of these portions can be used together in a single device.

Reservoirs can be fabricated in a structural body portion using any suitable fabrication technique known in the art. Representative fabrication techniques include MEMS fabrication processes, microfabrication processes, or other micromachining processes, various drilling techniques (e.g., laser, mechanical, and ultrasonic drilling), and build-up or lamination techniques, such as LTCC (low temperature co-fired ceramics). The surface of the reservoir optionally can be treated or coated to alter one or more properties of the surface. Examples of such properties include hydrophilicity/hydrophobicity, wetting properties (surface energies, contact angles, etc.), surface roughness, electrical charge, release characteristics, and the like. MEMS methods, micromolding, micromachining, and microfabrication techniques known in the art can be used to fabricate the substrate/reservoirs from a variety of materials. Numerous other methods known in the art can also be used to form the reservoirs. See, for example, U.S. Pat. No. 6,123,861 and U.S. Pat. No. 6,808,522. Various polymer forming techniques also may be used, e.g., injection molding, thermocompression molding, extrusion, etc.

In various embodiments, the body portion of the containment device comprises silicon, a metal, a ceramic, a polymer, or a combination thereof. Examples of suitable substrate materials include metals (e.g., titanium, stainless steel), ceramics (e.g., alumina, silicon nitride), semiconductors (e.g., silicon), glasses (e.g., Pyrex™, BPSG), and degradable and non-degradable polymers. Where only fluid tightness is required, the substrate may be formed of a polymeric material, rather than a metal or ceramic which would typically be required for gas hermeticity.

In a preferred embodiment, each reservoir is formed of hermetic materials (e.g., metals, silicon, glasses, ceramics) and is hermetically sealed by a reservoir cap. Desirably, the substrate material is biocompatible and suitable for long-term implantation into a patient. In a preferred embodiment, the substrate is formed of one or more hermetic materials. The substrate, or portions thereof, may be coated, encapsulated, or otherwise contained in a hermetic biocompatible material (e.g., inert ceramics, titanium, and the like) before use. Non-hermetic materials may be completely coated with a layer of a hermetic material. For example, a polymeric substrate could have a thin metal coating. If the substrate material is not biocompatible, then it can be coated with, encapsulated, or otherwise contained in a biocompatible material, such as poly(ethylene glycol), polytetrafluoroethylene-like materials, diamond-like carbon, silicon carbide, inert ceramics, alumina, titanium, and the like, before use. In one embodiment, the substrate is hermetic, that is impermeable (at least during the time of use of the reservoir device) to the molecules to be delivered and to surrounding gases or fluids (e.g., water, blood, electrolytes or other solutions). In another embodiment, the substrate is made of a material that degrades or dissolves over a defined period of time into biocompatible components. Examples of such materials include biocompatible polymers, such as poly(lactic acid)s, poly(glycolic acid)s, and poly(lactic-co-glycolic acid)s, as well as degradable poly(anhydride-co-imides).

The substrate can be formed into a range of shapes or shaped surfaces. It can, for example, have a planar or curved surface, which for example could be shaped to conform to an attachment surface. In various embodiments, the substrate or the containment device is in the form of a planar chip, a circular or ovoid disk, an elongated tube, a sphere, or a wire. The substrate can be flexible or rigid. In various embodiments, the reservoirs are discrete, non-deformable, and disposed in an array across one or more surfaces (or areas thereof) of an implantable medical device.

The substrate may consist of only one material, or may be a composite or multi-laminate material, that is, composed of several layers of the same or different substrate materials that are bonded together. Substrate portions (as in FIG. 1) can be, for example, silicon or another micromachined substrate or combination of micromachined substrates such as silicon and Pyrex glass, e.g., as described in U.S. patent application Ser. No. 09/665,303 or U.S. Pat. No. 6,527,762. In another embodiment, the substrate comprises multiple silicon wafers bonded together. In yet another embodiment, the substrate comprises a low-temperature co-fired ceramic (LTCC) or other ceramic such as alumina. In one embodiment, the body portion is the support for a microchip device. In one example, this substrate is formed of silicon.

Total substrate thickness and reservoir volume can be increased by bonding or attaching wafers or layers of substrate materials together. The device thickness may affect the volume of each reservoir and/or may affect the maximum number of reservoirs that can be incorporated onto a substrate. The size and number of substrates and reservoirs can be selected to accommodate the quantity and volume of reservoir contents needed for a particular application, manufacturing limitations, and/or total device size limitations to be suitable for implantation into a patient, preferably using minimally invasive procedures.

In a preferred embodiment for an implantable sensor application using a planar sensor, the substrate preferably is relatively thin, as noted above.

The substrate can have one, two, three or more reservoirs. In various embodiments, tens, hundreds, or thousands of reservoirs are arrayed across the substrate. For instance, one embodiment of an implantable drug delivery device includes between 250 and 750 reservoirs, where each reservoir contains a single dose of a drug for release. In one sensing embodiment, the number of reservoirs in the device is determined by the operation life of the individual sensors. For example, a one-year implantable glucose-monitoring device having individual sensors that remain functional for 30 days after exposure to the body would contain at least 12 reservoirs (assuming one sensor per reservoir). In another sensor embodiment, the distance between the sensor surface and the reservoir opening means is minimized, preferably approaching a few microns. In this case, the volume of the reservoir is primarily determined by the surface area of the sensor. For example, the electrodes of a typical enzymatic glucose sensor may occupy a space that is 400 µm by 800 µm.

In one embodiment, the reservoirs are microreservoirs. The "microreservoir" is a reservoir suitable for storing and releasing/exposing a microquantity of material, such as a drug formulation. In one embodiment, the microreservoir has a volume equal to or less than 500 µL (e.g., less than 250 µL, less than 100 µL, less than 50 µL, less than 25 µL, less than 10 µL, etc.) and greater than about 1 nL (e.g., greater than 5 nL, greater than 10 nL, greater than about 25 nL, greater than about 50 nL, greater than about 1 µL, etc.). The term "microquantity" refers to volumes from 1 nL up to 500 µL. In one embodiment, the microquantity is between 1 nL and 1 µL. In another embodiment, the microquantity is between 10 nL and 500 nL. In still another embodiment, the microquantity is between about 1 µL and 500 µL. The shape and dimensions of the microreservoir can be selected to maximize or minimize contact area between the drug material (or sensor or other reservoir contents) and the surrounding surface of the microreservoir.

In one embodiment, the reservoir is formed in a 200-micron thick substrate and has dimensions of 1.5 mm by 0.83 mm, for a volume of about 250 nL, not counting the volume that would be taken up by the support structures, which may be about 20 to about 50 microns thick.

In another embodiment, the reservoirs are macroreservoirs. The "macroreservoir" is a reservoir suitable for storing and releasing/exposing a quantity of material larger than a microquantity. In one embodiment, the macroreservoir has a volume greater than 500 µL (e.g., greater than 600 µL, greater than 750 µL, greater than 900 µL, greater than 1 mL, etc.) and less than 5 mL (e.g., less than 4 mL, less than 3 mL, less than 2 mL, less than 1 mL, etc.).

Unless explicitly indicated to be limited to either micro- or macro-scale volumes/quantities, the term "reservoir" is intended to encompass both.

In one embodiment, the device comprises a microchip chemical delivery device. In another embodiment, the device includes polymeric chips or devices composed of non-silicon based materials that might not be referred to as "microchips." In one embodiment, the device comprises an osmotic pump, for example, the DUROS™ osmotic pump technology (Alza Corporation) included in commercial devices such as a VIADUR™ implant (Bayer Healthcare Pharmaceuticals and Alza Corporation).

Reservoir Cap Supports

Reservoir cap supports can comprise substrate material, structural material, or coating material, or combinations thereof. Reservoir cap supports comprising substrate material may be formed in the same step as the reservoirs. The MEMS methods, microfabrication, micromolding, and micromachining techniques mentioned above could be used to fabricate the substrate/reservoirs, as well as reservoir cap supports, from a variety of substrate materials. Reservoir cap supports comprising structural material may also be formed by deposition techniques onto the substrate and then MEMS methods, microfabrication, micromolding, and micromachining techniques. Reservoir cap supports formed from coating material may be formed using known coating processes and tape masking, shadow masking, selective laser removal techniques, or other selective methods.

A reservoir may have several reservoir cap supports in various configurations over its reservoir contents. For example, one reservoir cap support may span from one side of the reservoir to the opposite side; another reservoir cap support may cross the first reservoir cap support and span the two other sides of the reservoir. In such an example, four reservoir caps could be supported over the reservoir.

In one embodiment for a sensor application (e.g., a glucose sensor), the reservoir (of a device, which can include only one or which may include two or more reservoirs) has three or more reservoir openings and corresponding reservoir caps.

The dimensions and geometry of the support structure can be varied depending upon the particular requirements of a specific application. For instance, the thickness, width, and cross-sectional shape (e.g., square, rectangular, triangular) of the support structures may be tailored for a particular drug release kinetics for a certain drug formulation or implantation site, etc.

Reservoir Contents

The reservoir contents are essentially any object or material that needs to be isolated (e.g., protected from) the environment outside of the reservoir until a selected point in time, when its release or exposure is desired. In various embodiments, the reservoir contents comprise (a quantity of) chemical molecules, a secondary device, or a combination thereof.

Proper functioning of certain reservoir contents, such as a catalyst or sensor, generally does not require release from the reservoir; rather their intended function, e.g., catalysis or sensing, occurs upon exposure of the reservoir contents to the environment outside of the reservoir after opening of the reservoir cap. Thus, the catalyst molecules or sensing component can be released or can remain immobilized within the open reservoir. Other reservoir contents such as drug molecules often may need to be released from the reservoir in order to pass from the device and be delivered to a site in vivo to exert a therapeutic effect on a patient. However, the drug molecules may be retained within the reservoirs for certain in vitro applications.

In several embodiments, hermeticity, which is typically defined as a maximum allowable transport rate of a particular molecule (such as helium or water) for a particular application, of the sealed reservoirs is required. That is, whether a reservoir is considered hermetic can vary among different applications of the device depending upon the particular demands of the application.

Chemical Molecules

The reservoir contents can include essentially any natural or synthetic, organic or inorganic molecules or mixtures thereof. The molecules may be in essentially any form, such as a pure solid or liquid, a gel or hydrogel, a solution, an emulsion, a slurry, or a suspension. The molecules of interest may be mixed with other materials to control or enhance the rate and/or time of release from an opened reservoir. In various embodiments, the molecules may be in the form of solid mixtures, including amorphous and crystalline mixed powders, monolithic solid mixtures, lyophilized powders, and solid interpenetrating networks. In other embodiments, the molecules are in liquid-comprising forms, such as solutions, emulsions, colloidal suspensions, slurries, or gel mixtures such as hydrogels.

In a preferred embodiment, the reservoir contents comprise a drug formulation. The drug formulation is a composition that comprises a drug. As used herein, the term "drug" includes any therapeutic or prophylactic agent (e.g., an active pharmaceutical ingredient or API). In one embodiment, the drug is provided in a solid form, particularly for purposes of maintaining or extending the stability of the drug over a commercially and medically useful time, e.g., during storage in a drug delivery device until the drug needs to be administered. The solid drug matrix may be in pure form or in the form of solid particles of another material in which the drug is contained, suspended, or dispersed. In one embodiment, the drug is formulated with an excipient material that is useful for accelerating release, e.g., a water-swellable material that can aid in pushing the drug out of the reservoir and through any tissue capsule over the reservoir.

In one embodiment, the drug is formulated with one or more excipients that facilitate transport through tissue capsules. Examples of such excipients include solvents such as DMSO or collagen- or fibrin-degrading enzymes.

The drug can comprise small molecules, large (i.e., macro-) molecules, or a combination thereof. In one embodiment, the large molecule drug is a protein or a peptide. In various other embodiments, the drug can be selected from amino acids, vaccines, antiviral agents, gene delivery vectors, interleukin inhibitors, immunomodulators, neurotropic factors, neuroprotective agents, antineoplastic agents, chemotherapeutic agents, polysaccharides, anti-coagulants (e.g., LMWH, pentasaccharides), antibiotics (e.g., immunosuppressants), analgesic agents, and vitamins. In one embodiment, the drug is a protein. Examples of suitable types of proteins include, glycoproteins, enzymes (e.g., proteolytic enzymes), hormones or other analogs (e.g., LHRH, steroids, corticosteroids, growth factors), antibodies (e.g., anti-VEGF antibodies, tumor necrosis factor inhibitors), cytokines (e.g., $\alpha$-, $\beta$-, or $\gamma$-interferons), interleukins (e.g., IL-2, IL-10), and diabetes/obesity-related therapeutics (e.g., insulin, exenatide, PYY, GLP-1 and its analogs). In one embodiment, the drug is a gonadotropin-releasing (LHRH) hormone analog, such as leuprolide. In another exemplary embodiment, the drug comprises parathyroid hormone, such as a human parathyroid hormone or its analogs, e.g., hPTH(1-84) or hPTH(1-34). In a further embodiment, the drug is selected from nucleosides, nucleotides, and analogs and conjugates thereof. In yet another embodiment, the drug comprises a peptide with natriuretic activity, such as atrial natriuretic peptide (ANP), B-type (or brain) natriuretic peptide (BNP), C-type natriuretic peptide (CNP), or dendroaspis natriuretic peptide (DNP). In still another embodiment, the drug is selected from diuretics, vasodilators, inotropic agents, anti-arrhythmic agents, $Ca^+$ channel blocking agents, anti-adrenergics/sympatholytics, and renin angiotensin system antagonists. In one embodiment, the drug is a VEGF inhibitor, VEGF antibody, VEGF antibody fragment, or another anti-angiogenic agent. Examples include an aptamer, such as MACUGEN™ (Pfizer/Eyetech) (pegaptanib sodium)) or LUCENTIS™ (Genetech/Novartis) (rhuFab VEGF, or ranibizumab), which could be used in the prevention of choroidal neovascularization (useful in the treatment of age-related macular degeneration or diabetic retinopathy). In yet a further embodiment, the drug is a prostaglandin, a prostacyclin, or another drug effective in the treatment of peripheral vascular disease.

In another embodiment, the drug includes a bone morphogenic protein (e.g., OP-1, BMP-2, etc.), a growth factor (FGF, IGF, TGF-$\beta$, etc.), or a combination thereof. In still another embodiment, the drug is an angiogenic agent, such as VEGF. In a further embodiment, the drug is an anti-inflammatory, such as dexamethasone. In one embodiment, a device includes both angiogenic agents and anti-inflammatory agents.

The reservoirs in one device can include a single drug or a combination of two or more drugs, and/or two or more transport enhancers, and can further include one or more pharmaceutically acceptable carriers. Two or more transport enhancers, angiogenic agents, anti-inflammatory agents, or combinations thereof, can be stored together and released from the same one or more reservoirs or they can each be stored in and released from different reservoirs.

For in vitro applications, the chemical molecules can be any of a wide range of molecules where the controlled release of a small (milligram to nanogram) amount of one or more molecules is required, for example, in the fields of analytic chemistry or medical diagnostics. Molecules can be effective as pH buffering agents, diagnostic reagents, and reagents in complex reactions such as the polymerase chain reaction or other nucleic acid amplification procedures. In various other embodiments, the molecules to be released are fragrances or scents, dyes or other coloring agents, sweeteners or other concentrated flavoring agents, or a variety of other compounds. In yet other embodiments, the reservoirs contain immobilized molecules. Examples include any chemical species which can be involved in a reaction, including reagents, catalysts (e.g., enzymes, metals, and zeolites), proteins (e.g., antibodies), nucleic acids, polysaccharides, cells, and polymers, as well as organic or inorganic molecules which can function as a diagnostic agent.

The drug or other molecules for release can be dispersed in a matrix material, to control the rate of release. This matrix material can be a "release system," as described in U.S. Pat. No. 5,797,898, the degradation, dissolution, or diffusion properties of which can provide a method for controlling the release rate of the chemical molecules.

Particularly for drugs, the release system may include one or more pharmaceutical excipients. The release system may provide a temporally modulated release profile (e.g., pulsatile release) when time variation in plasma levels is desired or a more continuous or consistent release profile when a constant plasma level as needed to enhance a therapeutic effect, for example. Pulsatile release can be achieved from an individual reservoir, from a plurality of reservoirs, or a combination thereof. For example, where each reservoir provides only a single pulse, multiple pulses (i.e. pulsatile release) are achieved by temporally staggering the single pulse release from each of several reservoirs. Alternatively, multiple pulses can be achieved from a single reservoir by incorporating several layers of a release system and other materials into a single reservoir. Continuous release can be achieved by incorporating a release system that degrades, dissolves, or allows diffusion of molecules through it over an extended period. In addition, continuous release can be approximated by releasing several pulses of molecules in rapid succession ("digital" release). The active release systems described herein can be used alone or on combination with passive release systems, for example, as described in U.S. Pat. No. 5,797,898. For example, the reservoir cap can be removed by active means to expose a passive release system, or a given substrate can include both passive and active release reservoirs.

In one embodiment, the drug formulation within a reservoir comprises layers of drug and non-drug material. After the active release mechanism has exposed the reservoir contents, the multiple layers provide multiple pulses of drug release due to intervening layers of non-drug. Such a strategy can be used to obtain complex release profiles.

Secondary Devices

As used herein, unless explicitly indicated otherwise, the term "secondary device" includes any device or a component thereof that can be located in a reservoir. In one embodiment, the secondary device is a sensor or sensing component thereof. As used herein, a "sensing component" includes a component utilized in measuring or analyzing the presence, absence, or change in a chemical or ionic species, energy, or one or more physical properties (e.g., pH, pressure) at a site. Types of sensors include biosensors, chemical sensors, physical sensors, or optical sensors. Secondary devices are further described in U.S. Pat. No. 6,551,838. In one embodiment, the sensor is a pressure sensor. See, e.g., U.S. Pat. No. 6,221,024, and U.S. Pat. No. 6,237,398, and U.S. Patent Application Publication No. 2004/0073137. Examples of sensing components include components utilized in measuring or analyzing the presence, absence, or change in a drug, chemical, or ionic species, energy (or light), or one or more physical properties (e.g., pH, pressure) at a site.

In still another embodiment, the sensor includes a cantilever-type sensor, such as those used for chemical detection. For example, see U.S. Patent Application Publication No. 2005/0005676, which is incorporated herein by reference.

In one embodiment, a device is provided for implantation in a patient (e.g., a human or other mammal) and the reservoir contents comprise at least one sensor indicative of a physiological condition in the patient. For example, the sensor could monitor the concentration of glucose, urea, calcium, or a hormone present in the blood, plasma, interstitial fluid, vitreous humor, or other bodily fluid of the patient.

Several options exist for receiving and analyzing data obtained with secondary devices located within the primary device, which can be a microchip device or another device. The primary devices may be controlled by local microprocessors or remote control. Biosensor information may provide input to the controller to determine the time and type of activation automatically, with human intervention, or a combination thereof. For example, the operation of the device can be controlled by an on-board (i.e., within the package) microprocessor. The output signal from the device, after conditioning by suitable circuitry if needed, will be acquired by the microprocessor. After analysis and processing, the output signal can be stored in a writeable computer memory chip, and/or can be sent (e.g., wirelessly) to a remote location away from the microchip. Power can be supplied to the microchip system locally by a battery or remotely by wireless transmission. See, e.g., U.S. Patent Application Publication No. 2002/0072784.

In one embodiment, a device is provided having reservoir contents that include drug molecules for release and a sensor/sensing component. For example, the sensor or sensing component can be located in a reservoir or can be attached to the device substrate. The sensor can operably communicate with the device, e.g., through a microprocessor, to control or modify the drug release variables, including dosage amount and frequency, time of release, effective rate of release, selection of drug or drug combination, and the like. The sensor or sensing component detects (or not) the species or property at the site of in vivo implantation and further may relay a signal to the microprocessor used for controlling release from the device. Such a signal could provide feedback on and/or finely control the release of a drug. In another embodiment, the device includes one or more biosensors (which may be sealed in reservoirs until needed for use) that are capable of detecting and/or measuring signals within the body of a patient.

In one variation, an implantable medical device includes reservoirs comprising a sensor, sealed as described herein, and a signal from the sensor is transmitted (by any number of means, including hardwire or telemetry) to a separate drug delivery device, which could be a wearable (i.e., external) or internal pump, the signal being used in the control of the dosing of the drug.

As used herein, the term "biosensor" includes sensing devices that transduce the chemical potential of an analyte of interest into an electrical signal (e.g., by converting a mechanical or thermal energy into an electrical signal), as well as electrodes that measure electrical signals directly or indirectly. For example, the biosensor may measure intrinsic electrical signals (EKG, EEG, or other neural signals), pressure, temperature, pH, or mechanical loads on tissue structures at various in vivo locations. The electrical signal from the biosensor can then be measured, for example by a microprocessor/controller, which then can transmit the information to a remote controller, another local controller, or both. For example, the system can be used to relay or record information on the patient's vital signs or the implant environment, such as drug concentration.

In one embodiment, the device contains one or more sensors for use in glucose monitoring and insulin control. Information from the sensor could be used to actively control insulin release from the same device or from a separate insulin delivery device (e.g., a conventional insulin pump, either an externally worn version or an implanted version). Other embodiments could sense other analytes and delivery other types of drugs in a similar fashion.

In one aspect, the device is adapted for use in the management of diabetes. For example, in one embodiment, the present containment devices are in the form of an implantable multi-reservoir device storing an array of glucose sensors and capable of transmitting (by wire or wirelessly) glucose readings to a handheld or worn glucose meter-type device, which permits the patient to manually administer insulin to themselves (e.g., by injection).

Reservoir Caps

As used herein, the term "reservoir cap" refers to a membrane, thin film, or other structure suitable for separating the contents of a reservoir from the environment outside of the reservoir. Selectively removing the reservoir caps or making them permeable will then expose the contents of the reservoir to the environment. As used herein, the term "environment" refers to the environment external the reservoirs, including biological fluids and tissues at a site of implantation, air, fluids, and particulates present during storage or in vitro use of a device incorporating the multi-cap reservoir system described herein.

In a preferred embodiment, a discrete reservoir cap completely covers one of the reservoir's openings. In another embodiment, a discrete reservoir cap covers two or more, but less than all, of the reservoir's openings.

In passive devices, the reservoir caps are formed from a material or mixture of materials that degrade, dissolve, or disintegrate over time, or that do not degrade dissolve, or disintegrate, but are permeable or become permeable to molecules or energy. Representative examples of reservoir cap materials include polymeric materials, and non-polymeric materials such as porous forms of metals, semiconductors, and ceramics. Passive semiconductor barrier layer materials include nanoporous or microporous silicon membranes.

In active devices, the reservoir cap includes any material that can be disintegrated or permeabilized in response to an applied stimulus (e.g., electric field or current, magnetic field, change in pH, or by thermal, chemical, electrochemical, or mechanical means). Examples of suitable reservoir cap materials include gold, titanium, platinum, tin, silver, copper, zinc, alloys, and eutectic materials such as gold-silicon and gold-tin eutectics. Any combination of passive or active barrier layers can be present in a single device.

In various embodiments, the reservoir caps are electrically conductive. In one embodiment, the reservoir caps are in the form of a thin metal film. In another embodiment, the reservoir caps are made of multiple metal layers, such as a multilayer/laminate structure of platinum/titanium/platinum. For example, the top and bottom layers could be selected for adhesion layers on (typically only over a portion of) the reservoir caps to ensure that the reservoir caps adhere to/bonds with both the substrate area around the reservoir openings, reservoir cap supports, and a dielectric overlayer. In one specific example, the structure is titanium/platinum/titanium/platinum/titanium, where the top and bottom layers serve as adhesion layers, and the platinum layers provide extra stability/biostability and protection to the main, central titanium layer. The thickness of these layers could be, for example, about 300 nm for the central titanium layer, about 40 nm for each of the platinum layers, and between about 10 and 15 nm for the adhesion titanium layers.

Control Means for Disintegrating or Permeabilizing the Reservoir Cap

The containment device includes control means that facilitates and controls reservoir opening, e.g., for disintegrating or permeabilizing the reservoir caps at a select time following sealing of the reservoirs as described herein. The control means comprises the structural component(s) and electronics (e.g., circuitry and power source) for powering and for controlling the time at which release or exposure of the reservoir contents is initiated.

The control means can take a variety of forms. In one embodiment, the reservoir cap comprises a metal film that is disintegrated by electrothermal ablation as described in U.S. Patent Application Publication No. 2004/0121486 A1, and the control means includes the hardware, electrical components, and software needed to control and deliver electric energy from a power source (e.g., battery, storage capacitor) to the selected reservoir caps for actuation, e.g., reservoir opening. For instance, the device can include a source of electric power for applying an electric current through an electrical input lead, an electrical output lead, and a reservoir cap connected therebetween in an amount effective to disintegrate the reservoir cap. Power can be supplied to the control means of the multi-cap reservoir system locally by a battery or (bio)fuel cell or remotely by wireless transmission, as described for example in U.S. Patent Application Publication No. 2002/0072784. In one embodiment, particularly for devices utilizing electrothermal ablation, the current source comprises a capacitor. It can be charged locally by an on-board battery or remotely, for example by an RF signal or ultrasound.

In one embodiment, the control means includes an input source, a microprocessor, a timer, a demultiplexer (or multiplexer). The timer and (de)multiplexer circuitry can be designed and incorporated directly onto the surface of the substrate during fabrication. In another embodiment, some of the components of the control means are provided as a separate component, which can be tethered or untethered to the reservoir portion of the device. For instance, the controller and/or power source may be physically remote from, but operably connected to and/or in communication with, the multi-cap reservoir device. In one embodiment, the operation of the multi-cap reservoir system will be controlled by an on-board (e.g., within an implantable device) microprocessor. In another embodiment, a simple state machine is used, as it typically is simpler, smaller, and/or uses less power than a microprocessor.

Other reservoir opening and release control methods are described in U.S. Pat. No. 5,797,898, U.S. Pat. No. 6,527,762, and U.S. Pat. No. 6,491,666, U.S. Patent Application Publication Nos. 2004/0121486, 2002/0107470 A1, 2002/0072784 A1, 2002/0138067 A1, 2002/0151776 A1, 2002/0099359 A1, 2002/0187260 A1, and 2003/0010808 A1; PCT WO 2004/022033 A2; PCT WO 2004/026281; and U.S. Pat. Nos. 5,797,898; 6,123,861; and 6,527,762, all of which are incorporated by reference herein.

Fabrication Methods

The basic methods of fabricating and assembling the devices described herein are known or can be adapted from techniques known in the art. See, for example, U.S. Pat. No. 5,797,898; U.S. Pat. No. 6,123,861; U.S. Pat. No. 6,527,762; U.S. Pat. No. 6,551,838; U.S. Patent Application Publication No. 2003/0010808; U.S. Patent Application Publication No. 2002/0099359; U.S. Patent Application Publication No. 2002/0107470; U.S. Patent Application Publication No. 2002/0151776; and U.S. Patent Application Publication No. 2004/0121486, which are hereby incorporated by reference in their entirety.

In one embodiment, the reservoir cap supports and reservoirs are fabricated simultaneously. The reservoir cap supports can be fabricated from the same material as the substrate. For example, the reservoir cap supports and reservoirs can be formed using MEMS fabrication, microfabrication, micromachining, or micromolding techniques known in the art.

One particular fabrication method useful for making the devices described herein includes a boron-doping step, and another particular fabrication method useful for making the devices described herein includes deep reactive ion etching (DRIE). Exemplary steps (fabrication sequences) for these methods are shown in FIGS. 6 and 7.

In another embodiment, the reservoir cap supports are formed in a separate step from the formation of the reservoirs and are fabricated from a structural material. For instance, one such structural material is polysilicon. The reservoir cap supports could be formed from structural material using photolithography and etching techniques. For example, the reservoir cap supports can be formed from structural material disposed on the substrate containing reservoirs as follows: Photoresist is patterned in the form of the reservoir openings that will be covered by the reservoir caps. The photoresist is developed such that the desired reservoir openings are left uncovered by the photoresist. The structural material is then etched using any know technique to create the reservoir cap supports. This process typically utilizes a sacrificial (i.e., removable) layer underneath the structural layer to temporarily support the reservoir cap after patterning the openings in the structural layer. For instance, one process that can be used to produce the device illustrated in FIG. 3 comprises the following steps:

(a) Deposit a sacrificial layer on the substrate;
(b) Deposit a structural layer over the sacrificial layer;
(c) Pattern the structural layer to create reservoir openings, for example by using photolithography and etching, to selectively remove structural layer but not sacrificial layer;

(d) Deposit and pattern reservoir cap material (e.g., Ti/Pt/Ti/Pt); and (e) From the opposite side of the substrate, remove the sacrificial layer from beneath the reservoir cap, for example by using an etching process to selectively remove the sacrificial layer but note the cap material or structural layer.

In yet another embodiment, the reservoir cap supports are formed of a coating material. Reservoir cap supports formed from coating material may be formed using known coating processes and tape masking, shadow masking, selective laser removal techniques, or other selective methods.

Using the Multi-Cap Reservoir Systems/Devices

The multi-cap reservoir release/exposure devices and systems described herein can be used in a wide variety of applications. Preferred applications include the controlled delivery of a drug, biosensing, or a combination thereof.

In a preferred embodiment, the multi-cap reservoir system is part of an implantable medical device. The implantable medical device can take a wide variety of forms and be used in a variety of therapeutic and/or diagnostic applications. In one embodiment, the reservoirs store and release a drug formulation over an extended period of time. For example, the device is implanted into a patient (such as a human or other vertebrate animal) using standard surgical or minimally invasive implantation techniques, and then the reservoirs are opened on a schedule determined by the type of drug therapy prescribed by the physician. Exemplary drug delivery applications include the delivery of potent molecules, including, hormones (e.g., PTH), steroids, cytokines, chemotherapeutics, growth factors, vaccines, gene delivery vectors, anti-VEGF aptamers, and certain analgesic agents.

In another embodiment, the store and contain a sensor for selective exposure, wherein the reservoirs are opened as needed (depending, for example, upon fouling of the sensor) or as dictated by a predetermined schedule. For example, the reservoirs could contain a pressure sensor, a chemical sensor, or a biological sensor. In a particular embodiment, the reservoirs comprise a glucose sensor, which may, for instance, comprise glucose oxidase immobilized on an electrode in the reservoir and coated with one or more permeable/semi-permeable membranes. Because the enzyme could lose its activity when exposed to the environment (e.g., the body) before its intended time of use, the sealed reservoir serves to protect the enzyme until it is needed.

In still another embodiment, the device is adapted for implantation into a patient suffering from congestive heart failure. In one example, the method of treatment includes the steps of (i) implanting a drug delivery module in a patient which can selectively release one or more drugs into the patient which are useful in the management or treatment of congestive heart failure; and (ii) releasing the one or more drugs from the implanted module, for example, in response to one or more monitored patient parameters (e.g., blood pressure, cardiac electrical signals, tissue electrical impedance, blood oxygen, blood oxygen saturation, natriuretic peptide levels, body weight, and combinations thereof). In one embodiment, the method further includes implanting a monitoring module in the patient and monitoring one or more patient parameters. Interaction of the drug delivery module and the monitoring module can be controlled by at least one microcontroller. In a preferred embodiment, the one or more drugs include a natriuretic peptide. Because some drugs can cause side effects such as hypotension, the monitoring module can monitor a patient parameter such as blood pressure as the drug is administered in small doses, essentially titrating the dose of drug to the patient.

In still other embodiments, the multi-cap reservoir systems and devices described herein are incorporated into a variety of other devices. For example, the hermetically sealed reservoirs could be integrated into other types and designs of implantable medical devices, such as the catheters and electrodes described in U.S. Patent Application Publication No. 2002/0111601. In another example, it could be incorporated into another medical device, in which the present devices and systems release drug into a carrier fluid that then flows to a desired site of administration, as illustrated for example in U.S. Pat. No. 6,491,666. The hermetically sealed reservoirs also could be incorporated into a drug pump, an inhaler or other pulmonary drug delivery device.

The multi-cap reservoir systems and devices described herein also have numerous in vitro and commercial diagnostic applications. The devices are capable of delivering precisely metered quantities of molecules and thus are useful for in vitro applications, such as analytical chemistry and medical diagnostics, as well as biological applications such as the delivery of factors to cell cultures. In still other non-medical applications, the devices are used to control release of fragrances, dyes, or other useful chemicals.

Still other applications are described in U.S. Pat. Nos. 5,797,898; 6,527,762; 6,491,666; and 6,551,838, and U.S. Patent Application Publications 2002/0183721, 2003/0100865, 2002/0099359, 2004/0082937, 2004/0127942, 2004/0121486, 2004/0106914, and 2004/0106953, all of which are incorporated by reference herein.

The invention can further be understood with reference to the following non-limiting examples.

EXAMPLE 1

Boron Diffusion Process for Making Multi-Opening and -Capped Reservoir Devices

Figure 11A:
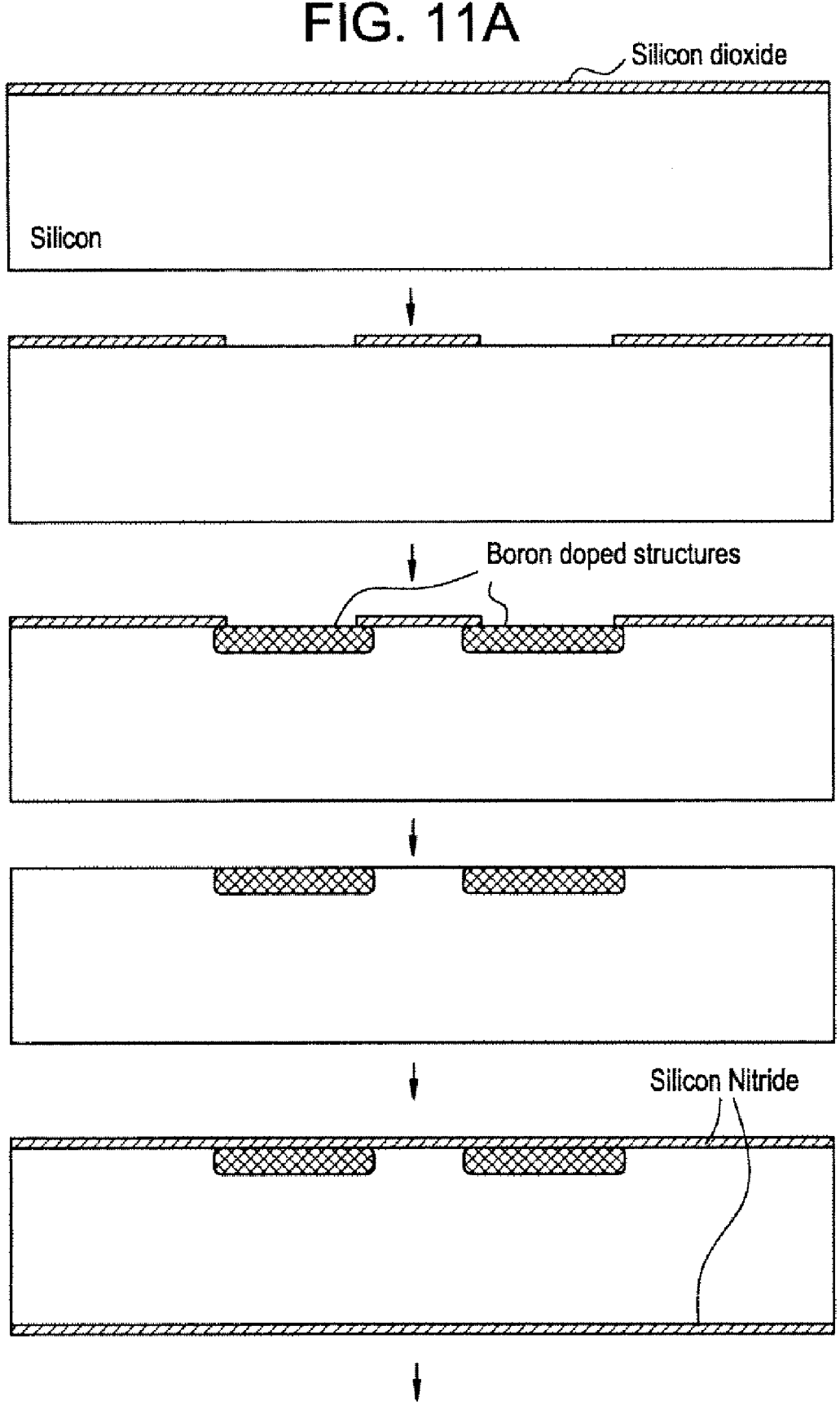
FIG. 11 is a process flow diagram of a boron diffusion process for making one embodiment of the devices described herein.
Figure 11B:
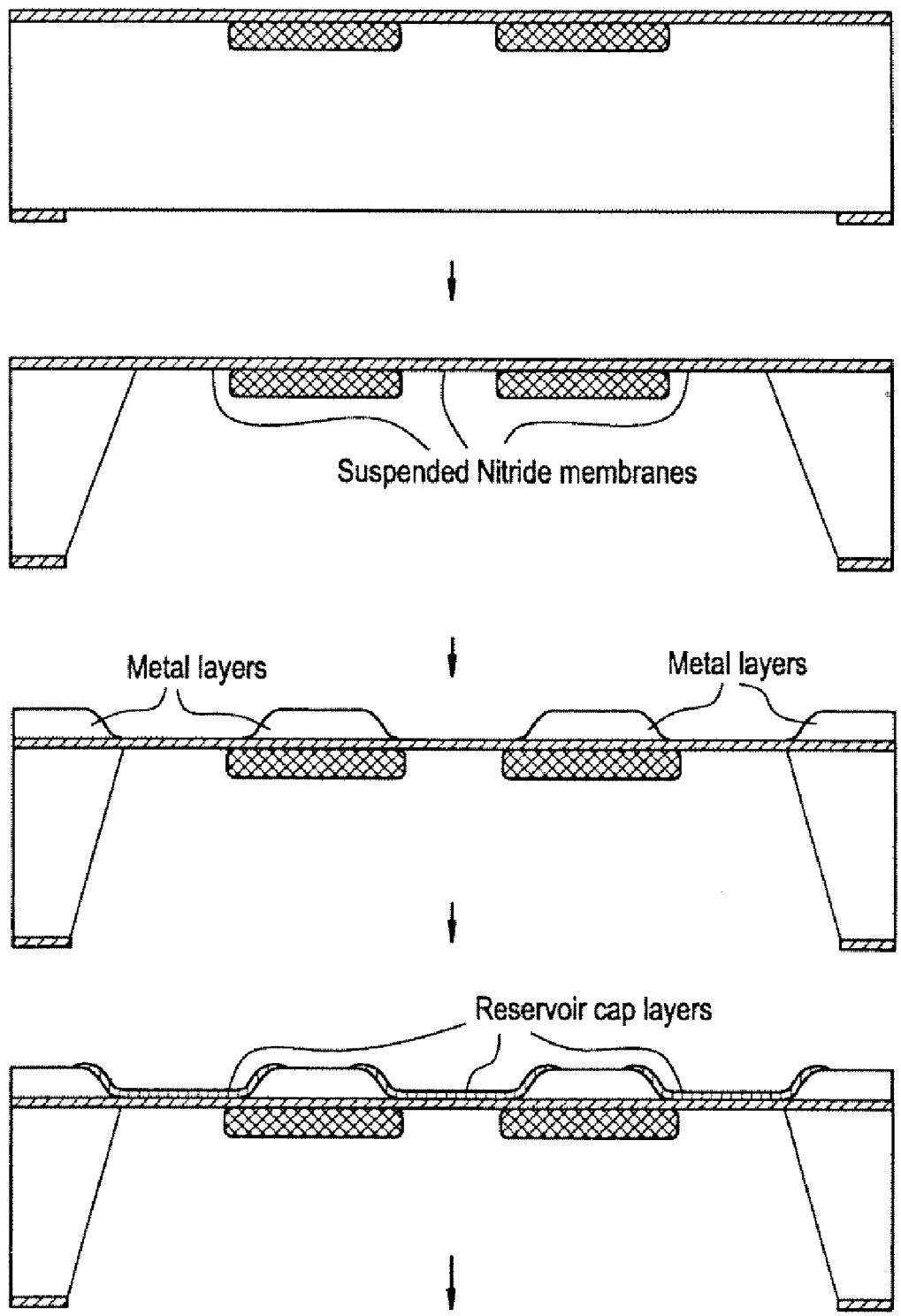
Figure 11C:
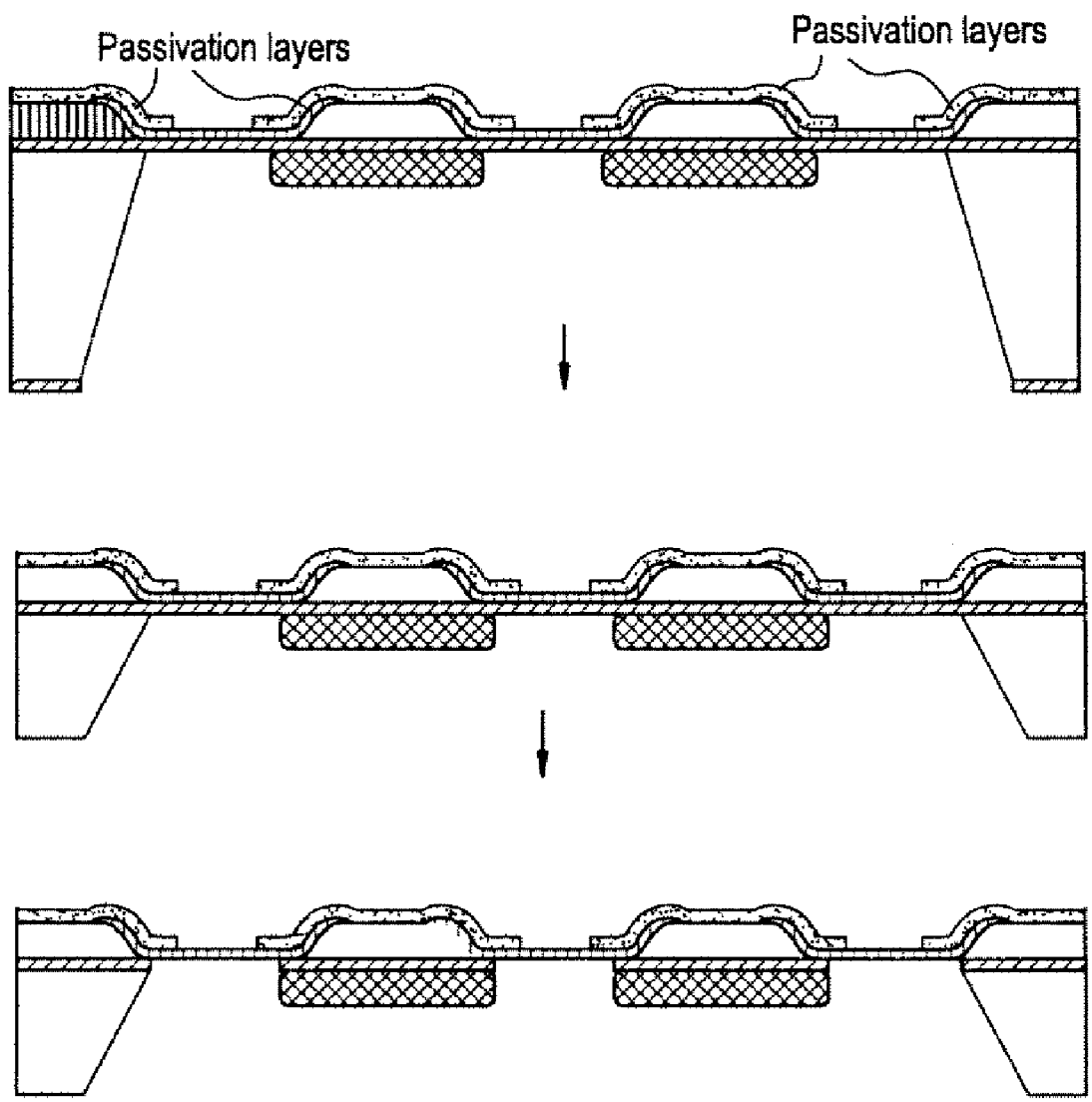

A boron diffusion process that has been used is illustrated in FIG. 11. The steps are as follows:

1) Thermal oxidation: deposit 2000 Å of silicon dioxide
2) Wet etch to pattern the thermal oxide
3) Boron diffusion or ion implantation
4) Wet etch to remove the oxide
5) Deposit 200 nm low stress nitride by LPCVD
6) Pattern nitride with photoresist
7) Etch nitride by RIE
8) Anisotropic etch of silicon using ethylene diamine/pyrocatechol (EDP), tetramethyl ammonium hydroxide (TMAH) or potassium hydroxide (KOH)
9) Deposit metal layer by sputtering. (Thickness: 12.5 nm Ti/2 μm Au).
10) Pattern metal layer with photoresist
11) Etch metal layer by dilute HF/Aqua Regia Au etch
12) Deposit and etch 12.5 nm Ti adhesion layer
13) Pattern reservoir cap layer for liftoff
14) Deposit reservoir cap layer by sputtering (sputter clean, lift off deposition)
15) Perform liftoff
16) Deposit and etch conformal coating layer to passivate the chip
17) Chemical and mechanical grinding and polishing to thin the silicon wafer
18) RIE Backside nitride etch

EXAMPLE 2

DRIE Process for Making Multi-Opening and -Capped Reservoir Devices

Figure 12A:
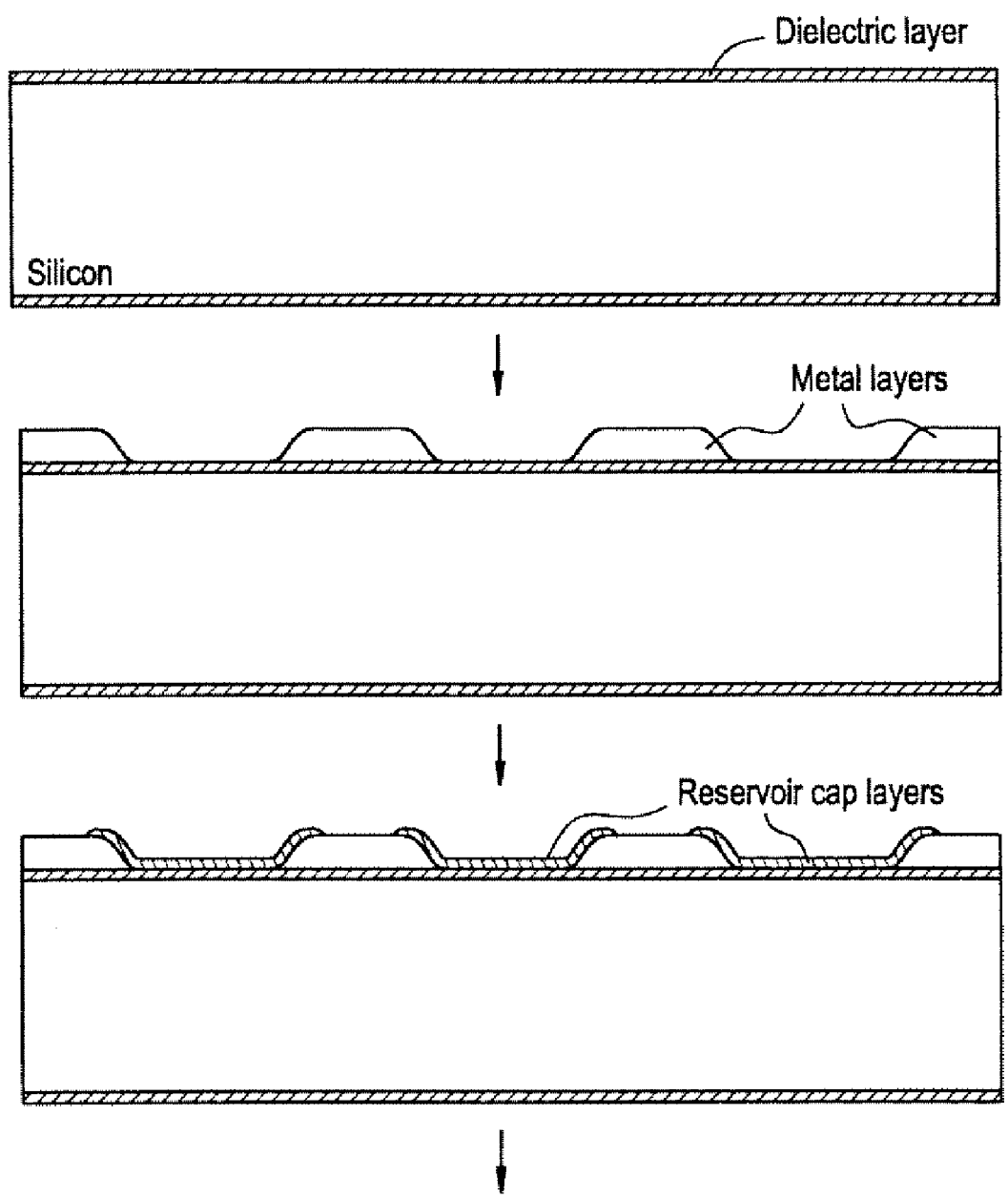
FIG. 12 is a process flow diagram of a DRIE process for making one embodiment of the devices described herein.
Figure 12B:
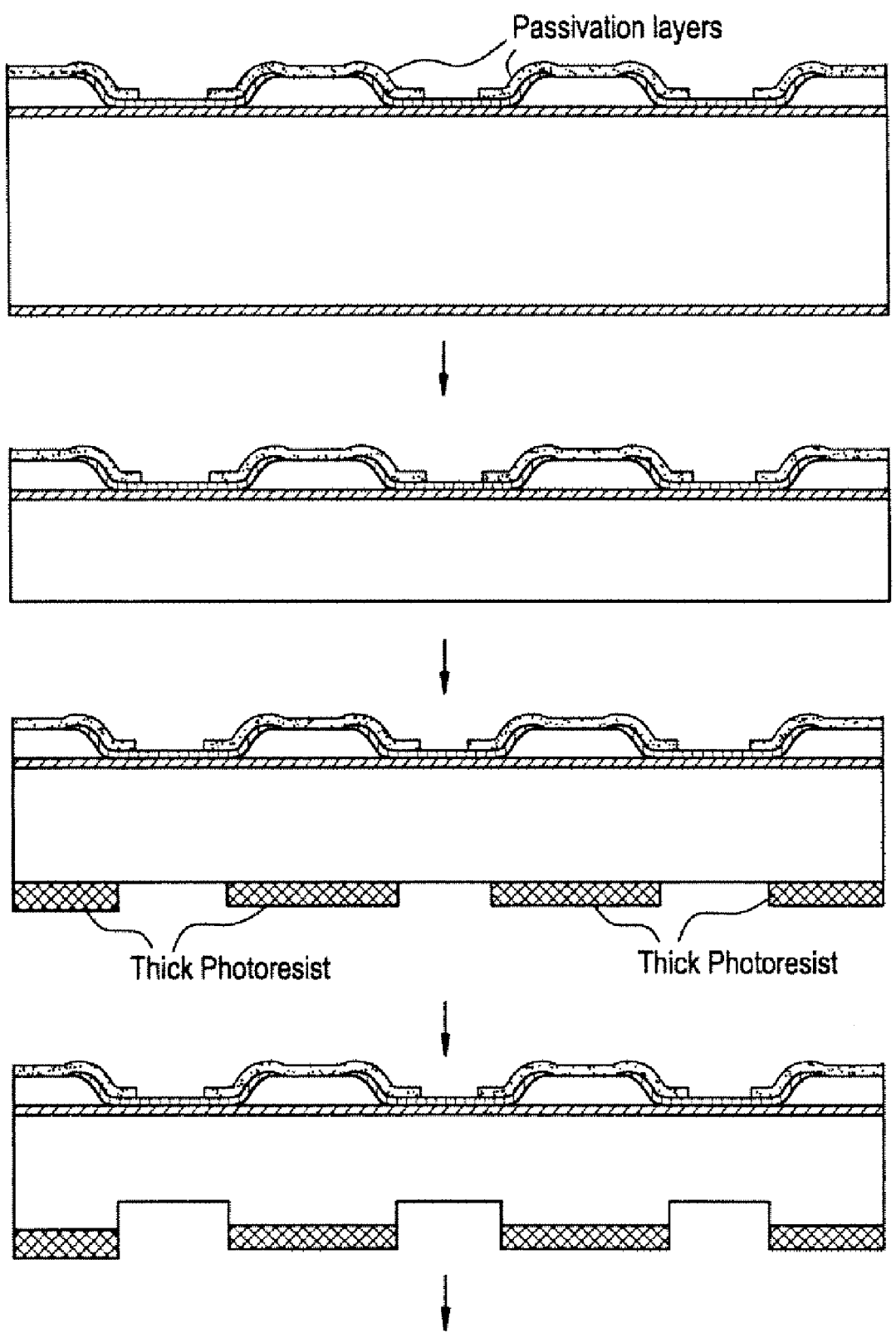
Figure 12C:
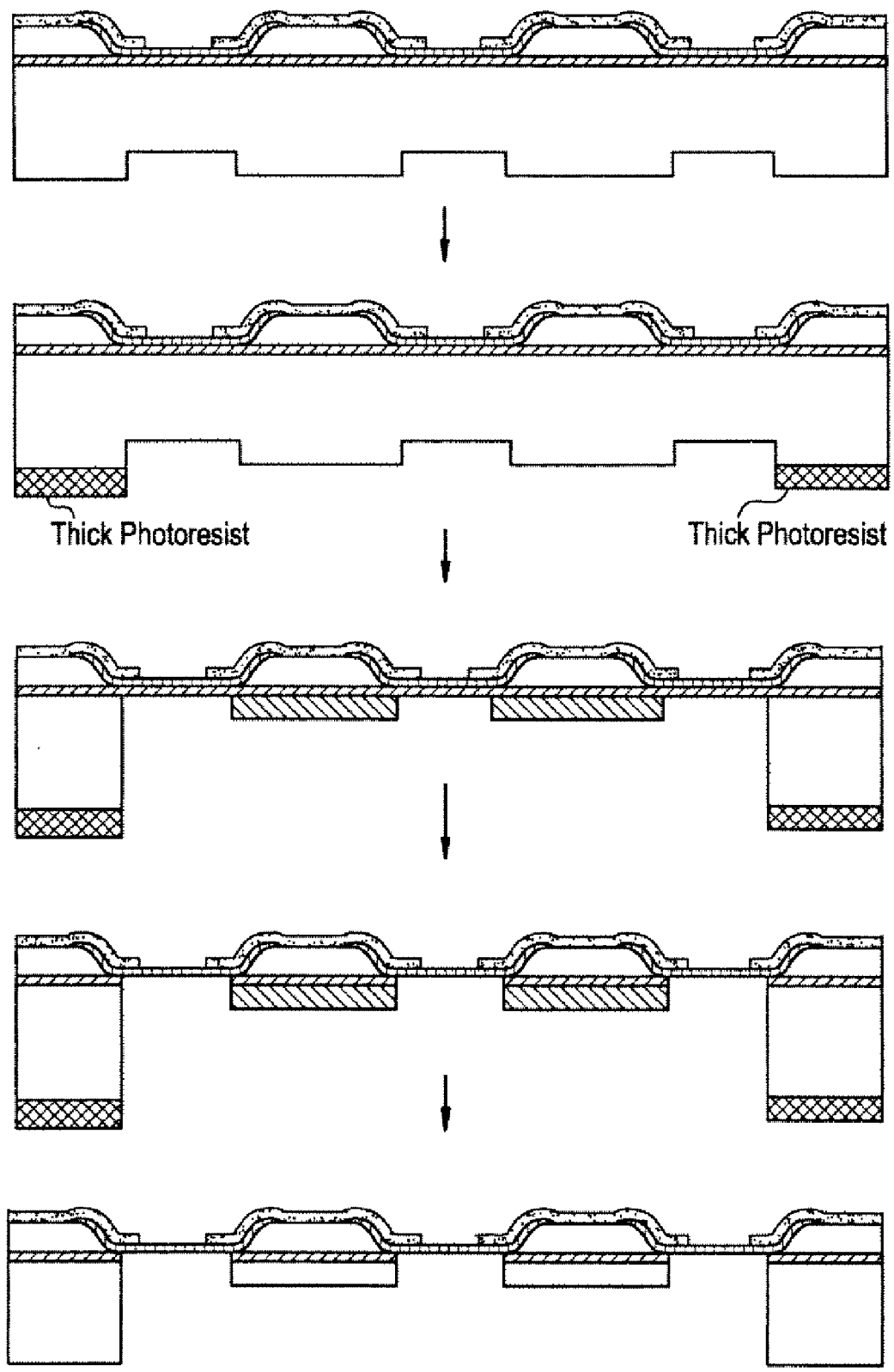

A Deep Reactive Ion Etch (DRIE) process that has been used is illustrated in FIG. 12. The steps are as follows:

1) Dielectric deposition: LPCVD Nitride and PECVD oxide

2) Deposit metal layer by sputtering (thickness: 12.5 nm Ti/2 μm Au).
3) Pattern metal layer with photoresist
4) Etch metal layer by dilute HF/Aqua Regia Au etch
5) Deposit and etch 12.5 nm Ti adhesion layer
6) Pattern reservoir cap layer for liftoff
7) Deposit reservoir cap layer by sputtering (sputter clean, lift off deposition)
8) Perform liftoff
9) Deposit and etch conformal coating layer to passivate the chip
10) Chemical and mechanical grinding and polishing to thin the silicon wafer
11) Thick photoresist deposition and patterning
12) DRIE etch
13) Remove photoresist
14) Thick photoresist deposition and patterning
15) DRIE etch
16) Dry and wet etch to etch backside dielectric layers
17) Remove photoresist Publications cited herein are incorporated by reference. Modifications and variations of the methods and devices described herein will be obvious to those skilled in the art from the foregoing detailed description. Such modifications and variations are intended to come within the scope of the appended claims.

We claim:

1. A method of permitting the ingress or egress of a substance to or from a medical device implanted in a patient, comprising:
    disintegrating a first reservoir cap portion covering a first opening of a containment reservoir defined by a substrate of the medical device; and
    disintegrating a second reservoir cap portion covering a second opening of the containment reservoir,
    wherein the first and second reservoir cap portions are positioned on an outer surface of the medical device.

2. The method of claim 1, wherein the first reservoir cap portion is a first discrete reservoir cap and the second reservoir cap portion is a second discrete reservoir cap.

3. The method of claim 1, wherein the disintegration of the first and second reservoir cap portions occurs simultaneously.

4. The method of claim 1, wherein the disintegration of the first and second reservoir cap portions occurs serially.

5. The method of claim 1, wherein the containment reservoir comprises a drug or a sensor.

6. The method of claim 1, wherein the containment reservoir comprises a drug and the drug is released from the first and second openings.

7. The method of claim 1, wherein the containment reservoir comprises a sensor.

8. The method of claim 1, wherein at least one reservoir cap support spans from one side to an opposed side of the containment reservoir between the first and second openings.

9. The method of claim 1, further comprising activating a control means to selectively disintegrate the first and second reservoir cap portions.

10. The method of claim 1, wherein the first and second reservoir cap portions are positioned on the same outer surface of the medical device.

11. The method of claim 1, wherein the containment reservoir is hermetically sealed.

12. A method of permitting the ingress or egress of a substance to or from a containment cavity of a medical device implanted in a patient, comprising:
    disintegrating a first cavity cap portion covering a first opening of the containment cavity; and
    disintegrating a second cavity cap portion covering a second opening of the containment cavity;
    wherein the first and second cavity cap portions are positioned on an outer surface of the medical device.

13. The method of claim 12, wherein the first cavity cap portion is a first discrete cavity cap and the second cavity cap portion is a second discrete cavity cap.

14. The method of claim 12, wherein the disintegration of the first and second cavity cap portions occurs simultaneously.

15. The method of claim 12, wherein the disintegration of the first and second cavity cap portions occurs serially.

16. The method of claim 12, wherein the containment cavity contains a drug and the drug is released from the first and second openings.

17. The method of claim 12, wherein the containment cavity contains a sensor.

18. The method of claim 12, wherein at least one cavity cap support spans from one side to an opposed side of the containment cavity between the first and second openings.

19. A method of controlled release or exposure of reservoir contents of a medical device, comprising:
    implanting the medical device in a patient, wherein a substrate of the medical device defines a containment reservoir having a first opening and a second opening;
    disintegrating a first reservoir cap portion covering the first opening to release or expose the reservoir contents; and
    disintegrating a second reservoir cap portion covering the second opening to release or expose the reservoir contents.

20. The method of claim 19, wherein the reservoir contents comprise a drug or a sensor.

* * * * *